US011360029B2

(12) United States Patent
Hassibi et al.

(10) Patent No.: US 11,360,029 B2
(45) Date of Patent: Jun. 14, 2022

(54) METHODS AND SYSTEMS FOR TIME-GATED FLUORESCENT-BASED DETECTION

(71) Applicant: InSilixa, Inc., Sunnyvale, CA (US)

(72) Inventors: Arjang Hassibi, Santa Clara, CA (US); Arun Manickam, San Jose, CA (US); Rituraj Singh, Sunnyvale, CA (US); Robert G. Kuimelis, Palo Alto, CA (US)

(73) Assignee: INSILIXA, INC., Sunnyvale, CA (US)

( * ) Notice: Subject to any disclaimer, the term of this patent is extended or adjusted under 35 U.S.C. 154(b) by 0 days.

(21) Appl. No.: 16/840,773

(22) Filed: Apr. 6, 2020

(65) Prior Publication Data
US 2020/0292457 A1 Sep. 17, 2020

Related U.S. Application Data

(63) Continuation of application No. PCT/US2020/022830, filed on Mar. 13, 2020.

(60) Provisional application No. 62/818,614, filed on Mar. 14, 2019.

(51) Int. Cl.
*G01N 21/64* (2006.01)
*H04N 5/3745* (2011.01)
*G01J 3/44* (2006.01)

(52) U.S. Cl.
CPC ........ *G01N 21/6486* (2013.01); *G01J 3/4406* (2013.01); *G01N 21/6408* (2013.01); *G01N 21/6454* (2013.01); *H04N 5/37452* (2013.01)

(58) Field of Classification Search
CPC ........... G01N 21/6486; G01N 21/6408; G01N 21/6454; G01J 3/4406; H04N 5/37452
See application file for complete search history.

(56) References Cited

U.S. PATENT DOCUMENTS

| 4,027,971 A | 6/1977 | Kolman et al. |
| 4,469,863 A | 9/1984 | Ts et al. |
| 4,539,295 A | 9/1985 | Blough, Jr. |
| 4,562,157 A | 12/1985 | Lowe et al. |
| 4,683,195 A | 7/1987 | Mullis et al. |
| 4,683,202 A | 7/1987 | Mullis |
| 4,711,955 A | 12/1987 | Ward et al. |

(Continued)

FOREIGN PATENT DOCUMENTS

| CN | 1250483 A | 4/2000 |
| CN | 1993617 A | 7/2007 |

(Continued)

OTHER PUBLICATIONS

Seo, Min-Woong, et al. "A 10 ps time-resolution CMOS image sensor with two-tap true-CDS lock-in pixels for fluorescence lifetime imaging." IEEE Journal of Solid-State Circuits 51.1 (2015): 141-154. (Year: 2016).*

(Continued)

*Primary Examiner* — Robert J Eom
(74) *Attorney, Agent, or Firm* — Wilson Sonsini Goodrich & Rosati

(57) ABSTRACT

The present disclosure provides methods, apparatus and systems for time-gated fluorescent-based detection. Time-based fluorescence analysis can be used in certain biochemical assays by measuring the emitted photon flux from fluorophores after an individual excitation pulse.

26 Claims, 16 Drawing Sheets

(56) References Cited

U.S. PATENT DOCUMENTS

| | | | |
|---|---|---|---|
| 4,994,373 | A | 2/1991 | Stavrianopoulos et al. |
| 5,034,506 | A | 7/1991 | Summerton et al. |
| 5,082,830 | A | 1/1992 | Brakel et al. |
| 5,130,238 | A | 7/1992 | Malek et al. |
| 5,210,015 | A | 5/1993 | Gelfand et al. |
| 5,216,141 | A | 6/1993 | Benner |
| 5,235,033 | A | 8/1993 | Summerton et al. |
| 5,270,184 | A | 12/1993 | Walker et al. |
| 5,310,652 | A | 5/1994 | Gelfand et al. |
| 5,322,770 | A | 6/1994 | Gelfand |
| 5,323,115 | A | 6/1994 | Werner, Jr. |
| 5,328,824 | A | 7/1994 | Ward et al. |
| 5,333,675 | A | 8/1994 | Mullis et al. |
| 5,386,023 | A | 1/1995 | Sanghvi et al. |
| 5,399,491 | A | 3/1995 | Kacian et al. |
| 5,407,800 | A | 4/1995 | Gelfand et al. |
| 5,409,818 | A | 4/1995 | Davey et al. |
| 5,449,767 | A | 9/1995 | Ward et al. |
| 5,455,166 | A | 10/1995 | Walker |
| 5,455,705 | A | 10/1995 | Gusinov |
| 5,466,348 | A | 11/1995 | Holm-Kennedy |
| 5,475,610 | A | 12/1995 | Atwood et al. |
| 5,476,928 | A | 12/1995 | Ward et al. |
| 5,480,784 | A | 1/1996 | Kacian et al. |
| 5,487,972 | A | 1/1996 | Gelfand et al. |
| 5,491,063 | A | 2/1996 | Fisher et al. |
| 5,538,848 | A | 7/1996 | Livak et al. |
| 5,571,673 | A | 11/1996 | Picone |
| 5,573,906 | A | 11/1996 | Bannwarth et al. |
| 5,599,668 | A | 2/1997 | Stimpson et al. |
| 5,602,240 | A | 2/1997 | Mesmaeker et al. |
| 5,627,054 | A | 5/1997 | Gillespie |
| 5,632,957 | A | 5/1997 | Heller et al. |
| 5,637,684 | A | 6/1997 | Cook et al. |
| 5,644,048 | A | 7/1997 | Yau et al. |
| 5,656,493 | A | 8/1997 | Mullis et al. |
| 5,674,698 | A | 10/1997 | Zarling et al. |
| 5,677,152 | A | 10/1997 | Birch et al. |
| 5,723,591 | A | 3/1998 | Livak et al. |
| 5,744,305 | A | 4/1998 | Fodor et al. |
| 5,773,258 | A | 6/1998 | Birch et al. |
| 5,789,224 | A | 8/1998 | Gelfand et al. |
| 5,804,375 | A | 9/1998 | Gelfand et al. |
| 5,807,522 | A | 9/1998 | Brown et al. |
| 5,837,501 | A | 11/1998 | Beumer et al. |
| 5,854,033 | A | 12/1998 | Lizardi |
| 5,871,928 | A | 2/1999 | Fodor et al. |
| 5,876,930 | A | 3/1999 | Livak et al. |
| 5,919,630 | A | 7/1999 | Nadeau et al. |
| 5,925,519 | A | 7/1999 | Jensen et al. |
| 5,955,351 | A | 9/1999 | Gerdes et al. |
| 5,974,164 | A | 10/1999 | Chee |
| 5,994,056 | A | 11/1999 | Higuchi |
| 6,025,601 | A | 2/2000 | Trulson et al. |
| 6,030,787 | A | 2/2000 | Livak et al. |
| 6,040,193 | A | 3/2000 | Winkler et al. |
| 6,048,690 | A | 4/2000 | Heller et al. |
| 6,054,270 | A | 4/2000 | Southern |
| 6,083,763 | A | 7/2000 | Balch |
| 6,103,476 | A | 8/2000 | Tyagi et al. |
| 6,110,426 | A | 8/2000 | Shalon et al. |
| 6,110,749 | A | 8/2000 | Obremski et al. |
| 6,114,122 | A | 9/2000 | Besemer et al. |
| 6,124,102 | A | 9/2000 | Fodor et al. |
| 6,127,155 | A | 10/2000 | Gelfand et al. |
| 6,153,425 | A | 11/2000 | Kozwich et al. |
| 6,169,981 | B1 | 1/2001 | Werbos |
| 6,171,785 | B1 | 1/2001 | Higuchi |
| 6,174,670 | B1 | 1/2001 | Wittwer et al. |
| 6,225,625 | B1 | 5/2001 | Pirrung et al. |
| 6,251,639 | B1 | 6/2001 | Kurn |
| 6,258,569 | B1 | 7/2001 | Livak et al. |
| 6,261,776 | B1 | 7/2001 | Pirrung et al. |
| 6,291,166 | B1 | 9/2001 | Gerdes et al. |
| 6,291,183 | B1 | 9/2001 | Pirrung et al. |
| 6,312,906 | B1 | 11/2001 | Cass et al. |
| 6,319,958 | B1 | 11/2001 | Johnson et al. |
| 6,327,410 | B1 | 12/2001 | Walt et al. |
| 6,330,092 | B1 | 12/2001 | Aronson |
| 6,365,729 | B1 | 4/2002 | Tyagi et al. |
| 6,391,550 | B1 | 5/2002 | Lockhart et al. |
| 6,403,341 | B1 | 6/2002 | Barnes et al. |
| 6,406,848 | B1 | 6/2002 | Bridgham et al. |
| 6,410,278 | B1 | 6/2002 | Notomi et al. |
| 6,428,957 | B1 | 8/2002 | Delenstarr |
| 6,432,695 | B1 | 8/2002 | Zou et al. |
| 6,465,175 | B2 | 10/2002 | Horn et al. |
| 6,469,524 | B1 | 10/2002 | Oberdier |
| 6,472,887 | B1 | 10/2002 | Tullis et al. |
| 6,516,276 | B1 | 2/2003 | Ghandour et al. |
| 6,593,091 | B2 | 7/2003 | Keys et al. |
| 6,600,996 | B2 | 7/2003 | Webster et al. |
| 6,610,482 | B1 | 8/2003 | Fodor et al. |
| 6,649,378 | B1 | 11/2003 | Kozwich et al. |
| 6,673,536 | B1 | 1/2004 | Stoughton et al. |
| 6,713,297 | B2 | 3/2004 | McMillan et al. |
| 6,724,324 | B1 | 4/2004 | Lambert |
| 6,743,581 | B1 | 6/2004 | Vo-Dinh |
| 6,744,502 | B2 | 6/2004 | Hoff et al. |
| 6,750,963 | B2 | 6/2004 | Sampas |
| 6,783,934 | B1 | 8/2004 | McMillan et al. |
| 6,806,052 | B2 | 10/2004 | Bridgham et al. |
| 6,814,934 | B1 | 11/2004 | Higuchi |
| 6,828,100 | B1 | 12/2004 | Ronaghi |
| 6,859,570 | B2 | 2/2005 | Walt et al. |
| 6,859,750 | B1 | 2/2005 | Frazier |
| 6,872,527 | B2 | 3/2005 | Gerdes et al. |
| 6,911,327 | B2 | 6/2005 | McMillan et al. |
| 6,942,971 | B2 | 9/2005 | McMillan et al. |
| 6,946,251 | B2 | 9/2005 | Kurn |
| 6,953,958 | B2 | 10/2005 | Baxter et al. |
| 6,969,488 | B2 | 11/2005 | Bridgham et al. |
| 7,060,431 | B2 | 6/2006 | Chee et al. |
| 7,064,197 | B1 | 6/2006 | Rabbani et al. |
| 7,087,387 | B2 | 8/2006 | Gerdes et al. |
| 7,122,355 | B2 | 10/2006 | Ankenbauer et al. |
| 7,145,645 | B2 | 12/2006 | Blumenfeld et al. |
| 7,223,540 | B2 | 5/2007 | Pourmand et al. |
| 7,291,496 | B2 | 11/2007 | Holm-Kennedy |
| 7,307,802 | B2 | 12/2007 | Unger |
| 7,317,216 | B2 | 1/2008 | Holm-Kennedy |
| 7,323,305 | B2 | 1/2008 | Leamon et al. |
| 7,348,141 | B2 | 3/2008 | French et al. |
| 7,361,472 | B2 | 4/2008 | Yguerabide et al. |
| 7,463,353 | B2 | 12/2008 | Yershov |
| 7,504,832 | B2 | 3/2009 | Kandori et al. |
| 7,588,672 | B2 | 9/2009 | Unger et al. |
| 7,599,060 | B2 | 10/2009 | Hoshizaki et al. |
| 7,622,294 | B2 | 11/2009 | Walt et al. |
| 7,630,227 | B2 | 12/2009 | Tran |
| 7,649,358 | B2 | 1/2010 | Toumazou et al. |
| 7,686,929 | B2 | 3/2010 | Toumazou et al. |
| 7,687,260 | B2 | 3/2010 | Gutekunst |
| 7,738,086 | B2 | 6/2010 | Shepard et al. |
| 7,785,776 | B2 | 8/2010 | Wittwer et al. |
| 7,785,785 | B2 | 8/2010 | Pourmand et al. |
| 7,824,890 | B2 | 11/2010 | Hoser et al. |
| 7,835,871 | B2 | 11/2010 | Kain et al. |
| 7,842,457 | B2 | 11/2010 | Berka et al. |
| 7,884,398 | B2 | 2/2011 | Levon et al. |
| 7,888,013 | B2 | 2/2011 | Miyahara et al. |
| 7,888,015 | B2 | 2/2011 | Toumazou et al. |
| 7,906,072 | B2 | 3/2011 | Unger et al. |
| 7,914,981 | B2 | 3/2011 | Barany et al. |
| 7,932,034 | B2 | 4/2011 | Esfandyarpour et al. |
| 7,948,015 | B2 | 5/2011 | Rothberg et al. |
| 7,995,679 | B2 | 8/2011 | Ranganathan et al. |
| 7,998,673 | B2 | 8/2011 | French et al. |
| 8,012,756 | B2 | 9/2011 | Pourmand et al. |
| 8,048,626 | B2 | 11/2011 | Hassibi et al. |
| 8,119,345 | B2 | 2/2012 | Weusten et al. |
| 8,158,359 | B2 | 4/2012 | Leamon et al. |
| 8,306,757 | B2 | 11/2012 | Rothberg et al. |
| 8,313,907 | B2 | 11/2012 | Pourmand et al. |

(56) References Cited

U.S. PATENT DOCUMENTS

| | | |
|---|---|---|
| 8,517,329 B2 | 8/2013 | Nash et al. |
| 8,518,329 B2 | 8/2013 | Hassibi et al. |
| 8,637,436 B2 | 1/2014 | Hassibi et al. |
| 8,735,067 B2 | 5/2014 | Zhang et al. |
| 8,790,876 B2 | 7/2014 | Leamon et al. |
| 8,969,781 B2 | 3/2015 | Hassibi et al. |
| 8,999,724 B2 | 4/2015 | Holt et al. |
| 9,040,237 B2 | 5/2015 | Koo et al. |
| 9,133,504 B2 | 9/2015 | Hassibi et al. |
| 9,223,929 B2 | 12/2015 | Hassibi et al. |
| 9,341,589 B2 | 5/2016 | Hassibi et al. |
| 9,377,388 B2 | 6/2016 | Walt et al. |
| 9,458,497 B2 | 10/2016 | Hassibi et al. |
| 9,465,002 B2 | 10/2016 | Hassibi et al. |
| 9,499,861 B1 | 11/2016 | Hassibi et al. |
| 9,708,647 B2 | 7/2017 | Hassibi et al. |
| 9,983,163 B2 | 5/2018 | Hassibi et al. |
| 10,174,367 B2 | 1/2019 | Hassibi et al. |
| 10,501,778 B2 | 12/2019 | Hassibi et al. |
| 2001/0030290 A1 | 10/2001 | Stern |
| 2001/0046673 A1 | 11/2001 | French et al. |
| 2002/0001844 A1 | 1/2002 | Frutos et al. |
| 2002/0006619 A1 | 1/2002 | Cohen et al. |
| 2002/0034746 A1 | 3/2002 | McMillan et al. |
| 2002/0102567 A1 | 8/2002 | Fodor et al. |
| 2002/0106653 A1 | 8/2002 | Kurane et al. |
| 2002/0119462 A1 | 8/2002 | Mendrick et al. |
| 2002/0123048 A1 | 9/2002 | Gau |
| 2002/0131899 A1 | 9/2002 | Kovacs |
| 2002/0146745 A1 | 10/2002 | Natan et al. |
| 2002/0150917 A1 | 10/2002 | Weidenhammer et al. |
| 2002/0177157 A1 | 11/2002 | Luo et al. |
| 2002/0187477 A1 | 12/2002 | Xue et al. |
| 2003/0040000 A1 | 2/2003 | Connolly et al. |
| 2003/0071843 A1 | 4/2003 | Hoff et al. |
| 2003/0130973 A1 | 7/2003 | Sumner et al. |
| 2003/0143591 A1 | 7/2003 | Davies et al. |
| 2003/0157581 A1 | 8/2003 | Grill et al. |
| 2003/0186310 A1 | 10/2003 | Kincaid |
| 2003/0194726 A1 | 10/2003 | Bolchakova et al. |
| 2003/0225718 A1 | 12/2003 | Shmulevich et al. |
| 2004/0002073 A1 | 1/2004 | Li et al. |
| 2004/0005582 A1 | 1/2004 | Shipwash |
| 2004/0038420 A1 | 2/2004 | Gelbart et al. |
| 2004/0053254 A1 | 3/2004 | Wangh et al. |
| 2004/0058378 A1 | 3/2004 | Kong et al. |
| 2004/0077648 A1 | 4/2004 | Timmer et al. |
| 2004/0080629 A1 | 4/2004 | Sato et al. |
| 2004/0081974 A1 | 4/2004 | Gao |
| 2004/0086864 A1 | 5/2004 | Lo et al. |
| 2004/0087033 A1 | 5/2004 | Schembri |
| 2004/0091862 A1 | 5/2004 | Brandenburg et al. |
| 2004/0096819 A1 | 5/2004 | McMillan et al. |
| 2004/0110219 A1 | 6/2004 | Buchholz et al. |
| 2004/0147045 A1 | 7/2004 | Nelson |
| 2004/0208792 A1 | 10/2004 | Linton et al. |
| 2004/0265902 A1 | 12/2004 | Fricker et al. |
| 2005/0003355 A1 | 1/2005 | Lu et al. |
| 2005/0064452 A1 | 3/2005 | Schmid et al. |
| 2005/0065290 A1 | 3/2005 | Shah |
| 2005/0084881 A1 | 4/2005 | Kelley et al. |
| 2005/0084884 A1 | 4/2005 | Palombella et al. |
| 2005/0089924 A1 | 4/2005 | Ho et al. |
| 2005/0112585 A1 | 5/2005 | Zichi et al. |
| 2005/0112634 A1 | 5/2005 | Woudenberg et al. |
| 2005/0161192 A1 | 7/2005 | Shigeura et al. |
| 2005/0202470 A1 | 9/2005 | Sundberg et al. |
| 2005/0238123 A1 | 10/2005 | Ranganathan et al. |
| 2005/0255516 A1 | 11/2005 | McMillan et al. |
| 2006/0014151 A1 | 1/2006 | Ogura et al. |
| 2006/0014200 A1 | 1/2006 | McMillan et al. |
| 2006/0024707 A1 | 2/2006 | Deans et al. |
| 2006/0051788 A1 | 3/2006 | Suzuki et al. |
| 2006/0068378 A1 | 3/2006 | Mirkin et al. |
| 2006/0078929 A1 | 4/2006 | Bickel et al. |
| 2006/0084069 A1 | 4/2006 | Chan et al. |
| 2006/0088844 A1 | 4/2006 | Xu |
| 2006/0094108 A1 | 5/2006 | Yoder et al. |
| 2006/0123516 A1 | 6/2006 | Ronen et al. |
| 2006/0208254 A1 | 9/2006 | Goodman et al. |
| 2006/0269922 A1 | 11/2006 | Sagner et al. |
| 2006/0269934 A1 | 11/2006 | Woudenberg et al. |
| 2007/0010664 A1 | 1/2007 | Thomas et al. |
| 2007/0026421 A1 | 2/2007 | Sundberg et al. |
| 2007/0057159 A1 | 3/2007 | Hing |
| 2007/0065818 A1 | 3/2007 | Foti et al. |
| 2007/0077609 A1 | 4/2007 | Gambhir et al. |
| 2007/0099198 A1 | 5/2007 | Hassibi et al. |
| 2007/0212681 A1 | 9/2007 | Shapiro et al. |
| 2007/0218610 A1 | 9/2007 | Lim et al. |
| 2007/0279631 A1 | 12/2007 | Yershov |
| 2008/0027008 A1 | 1/2008 | Henkin |
| 2008/0037008 A1 | 2/2008 | Shepard et al. |
| 2008/0039339 A1 | 2/2008 | Hassibi et al. |
| 2008/0081769 A1 | 4/2008 | Hassibi |
| 2008/0085839 A1 | 4/2008 | Klapproth |
| 2008/0176757 A1 | 7/2008 | Hassibi et al. |
| 2008/0305481 A1 | 12/2008 | Whitman et al. |
| 2009/0062134 A1 | 3/2009 | Linton et al. |
| 2009/0062152 A1 | 3/2009 | Linton et al. |
| 2009/0079414 A1 | 3/2009 | Levon et al. |
| 2009/0111207 A1 | 4/2009 | Choumane et al. |
| 2009/0137418 A1 | 5/2009 | Miller et al. |
| 2009/0143233 A1 | 6/2009 | Knight et al. |
| 2009/0143237 A1 | 6/2009 | Stender et al. |
| 2009/0156415 A1 | 6/2009 | Remacle et al. |
| 2009/0156425 A1 | 6/2009 | Walt et al. |
| 2009/0170728 A1 | 7/2009 | Walt et al. |
| 2009/0221025 A1 | 9/2009 | Huebner et al. |
| 2009/0318306 A1 | 12/2009 | Hasson et al. |
| 2009/0318307 A1 | 12/2009 | Garcia |
| 2009/0325164 A1 | 12/2009 | Vossenaar et al. |
| 2009/0325184 A1 | 12/2009 | Woudenberg et al. |
| 2010/0003715 A1 | 1/2010 | Pellegrino |
| 2010/0041030 A1 | 2/2010 | Hartwich |
| 2010/0105033 A1 | 4/2010 | Sun et al. |
| 2010/0122904 A1 | 5/2010 | Hassibi et al. |
| 2010/0129871 A1 | 5/2010 | Liu et al. |
| 2010/0137166 A1 | 6/2010 | Kain et al. |
| 2010/0138162 A1 | 6/2010 | Kain et al. |
| 2010/0233680 A1 | 9/2010 | Taylor et al. |
| 2010/0240544 A1 | 9/2010 | Liu et al. |
| 2010/0300899 A1 | 12/2010 | Levine et al. |
| 2010/0330578 A1 | 12/2010 | Duhr et al. |
| 2011/0009278 A1 | 1/2011 | Kain et al. |
| 2011/0009296 A1 | 1/2011 | Kain et al. |
| 2011/0086361 A1 | 4/2011 | Klunder et al. |
| 2011/0092692 A1 | 4/2011 | Jiang |
| 2011/0111968 A1 | 5/2011 | Okura et al. |
| 2011/0213252 A1 | 9/2011 | Fulghum |
| 2011/0236983 A1 | 9/2011 | Beechem et al. |
| 2011/0312810 A1 | 12/2011 | Moini et al. |
| 2012/0040853 A1 | 2/2012 | Pierik et al. |
| 2012/0052563 A1 | 3/2012 | Liang et al. |
| 2012/0077692 A1 | 3/2012 | Hassibi et al. |
| 2012/0088682 A1 | 4/2012 | Rothberg et al. |
| 2012/0094298 A1 | 4/2012 | Seul et al. |
| 2012/0115214 A1 | 5/2012 | Battrell et al. |
| 2012/0164652 A1 | 6/2012 | Clemens et al. |
| 2012/0168306 A1 | 7/2012 | Hassibi et al. |
| 2012/0295805 A1 | 11/2012 | Levicky et al. |
| 2013/0210656 A1 | 8/2013 | Wangh et al. |
| 2013/0225441 A1 | 8/2013 | Hassibi |
| 2013/0252827 A1 | 9/2013 | Chun |
| 2013/0345065 A1 | 12/2013 | Hassibi et al. |
| 2014/0001341 A1 | 1/2014 | Hassibi et al. |
| 2014/0162266 A1 | 6/2014 | Klitgord et al. |
| 2014/0272978 A1 | 9/2014 | Shi et al. |
| 2014/0287420 A1 | 9/2014 | Cadle-Davidson |
| 2014/0287428 A1 | 9/2014 | Sietze |
| 2014/0363821 A1 | 12/2014 | Bashir et al. |
| 2015/0093849 A1 | 4/2015 | Shepard et al. |
| 2015/0125855 A1 | 5/2015 | Li et al. |
| 2016/0160271 A1 | 6/2016 | Hassibi et al. |

(56) References Cited

U.S. PATENT DOCUMENTS

| | | |
|---|---|---|
| 2016/0231270 A1 | 8/2016 | Hassibi et al. |
| 2017/0081714 A1 | 3/2017 | Hassibi et al. |
| 2017/0362648 A1 | 12/2017 | Hassibi et al. |
| 2018/0251828 A1 | 9/2018 | Hassibi et al. |
| 2018/0251829 A1 | 9/2018 | Hassibi et al. |
| 2018/0335399 A1 | 11/2018 | Hassibi et al. |
| 2019/0062819 A1 | 2/2019 | Hassibi |
| 2019/0323070 A1 | 10/2019 | Hassibi et al. |

FOREIGN PATENT DOCUMENTS

| | | |
|---|---|---|
| EP | 0684315 A1 | 11/1995 |
| EP | 0236069 B1 | 5/1997 |
| EP | 0872562 A1 | 10/1998 |
| EP | 1608952 A2 | 12/2005 |
| EP | 1681557 A1 | 7/2006 |
| EP | 1754257 A2 | 2/2007 |
| EP | 1924681 A2 | 5/2008 |
| EP | 2126765 A1 | 12/2009 |
| EP | 2374902 A1 | 10/2011 |
| EP | 2489745 A2 | 8/2012 |
| EP | 2029775 B1 | 10/2014 |
| WO | WO-0079009 A2 | 12/2000 |
| WO | WO-0121838 A2 | 3/2001 |
| WO | WO-0186001 A1 | 11/2001 |
| WO | WO-0079009 A3 | 1/2002 |
| WO | WO-0230946 A1 | 4/2002 |
| WO | WO-02099397 A2 | 12/2002 |
| WO | WO-03062791 A2 | 7/2003 |
| WO | WO-2004011144 A2 | 2/2004 |
| WO | WO-03062791 A3 | 6/2004 |
| WO | WO-2004059006 A1 | 7/2004 |
| WO | WO-2005118870 A2 | 12/2005 |
| WO | WO-2005121159 A1 | 12/2005 |
| WO | WO-2006014351 A2 | 2/2006 |
| WO | WO-2006037527 A1 | 4/2006 |
| WO | WO-2006053769 A1 | 5/2006 |
| WO | WO-2007045755 A1 | 4/2007 |
| WO | WO-2007133703 A2 | 11/2007 |
| WO | WO-2007143669 A2 | 12/2007 |
| WO | WO-2008014485 A2 | 1/2008 |
| WO | WO-2008082713 A2 | 7/2008 |
| WO | WO-2008142571 A2 | 11/2008 |
| WO | WO-2008143646 A2 | 11/2008 |
| WO | WO-2009021054 A2 | 2/2009 |
| WO | WO-2009082706 A1 | 7/2009 |
| WO | WO-2009158451 A1 | 12/2009 |
| WO | WO-2011066186 A1 | 6/2011 |
| WO | WO-2013081987 A1 | 6/2013 |
| WO | WO-2013152203 A1 | 10/2013 |
| WO | WO-2016154227 A1 | 9/2016 |
| WO | WO-2017044100 A1 | 3/2017 |
| WO | WO-2017155858 A1 | 9/2017 |
| WO | WO-2018050501 A1 | 3/2018 |
| WO | WO-2020186252 A1 | 9/2020 |

OTHER PUBLICATIONS

Potrich, Cristina, et al. "On chip micro-extraction and real-time PCR with integrated SPAD optical fluorescence detection for nucleic acid analysis." Lab-on-a-Chip European Congress. 2011. (Year: 2011).*

Huang, Xiwei, et al. "A single-frame superresolution algorithm for lab-on-a-chip lensless microfluidic imaging." IEEE Design & Test 32.6 (2015): 32-40. (Year: 2015).*

A. Hassibi et al., 2018. Multiplexed identification, quantification and genotyping of infectious agents using a semiconductor biochip. Nature biotechnology, 36(8), p. 738.

Brodsky, et al. Identification and handling of artifactual gene expression profiles emerging in microarray hybridization experiments. Nucleic Acids Res. Mar. 3, 2004;32(4):e46.

Brown, et al. Exploring the new world of the genome with DNA microarrays. Nature Genet. 1999; 21 (Suppl.):33-37.

Cady, et al. Real-time PCR detection of Listeria monocytogenes using an integrated microfluidics platform. Sensors and Actuators B: Chemical. 2005; 107: 332-341.

Canon. High resolution thermal melt analysis. http://culs.canon.com/Science/Technology_Overview/High_Resolution_thermal_melt_analysis/High_Resolution_Thermal_Melt_Analysis.shtml. Accessed on Jun. 10, 2015. 1 pg.

Co-pending U.S. Appl. No. 16/191,836, filed Nov. 15, 2018.

Cronin, et al. Cystic fibrosis mutation detection by hybridization to light-generated DNA probe arrays. Hum Mutat. 1996;7(3):244-55.

Didenko. DNA probes using fluorescence resonance energy transfer (FRET): designs and applications. Biotechniques. Nov. 2001;31(5):1106-16, 1118, 1120-1.

Dolganov, et al. Novel molecular diagnostic (MDx) Platform for Highly-Multiplex Drug Susceptibility Testing of M. tuberculosis. http://www.stoptb.org/wg/new_diagnostics/assets/documents/09-NDWG-Annual-Meeting_GarySCHOOLNIK_&_Gregory_DOLGANOV.pdf. Accessed on Jun. 10, 2015. 13 pgs.

El Gamal, A., Dec. 2002. Trends in CMOS image sensor technology and design. In Digest. International Electron Devices Meeting, (pp. 805-808). IEEE.

El Gamal, et al. CMOS image sensors. Circuits and Devices Magazine, IEEE. 2005; 20(3):6-20.

FDA. Response to Section 501(k) Premarket Notification of Intent to Market. Re: K143178. Dated Jan. 30, 2015. 9 pages.

Field, R.M., Realov, S. and Shepard, K.L., 2014. A 100 fps, time-correlated single-photon-counting-based fluorescence-lifetime imager in 130 nm CMOS. IEEE Journal of Solid-State Circuits, 49(4), pp. 867-880.

Fossum, E.R. and Hondongwa, D.B., 2014. A review of the pinned photodiode for CCD and CMOS image sensors. IEEE J. Electron Devices Soc., 2(3), pp. 33-43.

Ginzinger. Gene quantification using real-time quantitative PCR: an emerging technology hits the mainstream. Exp Hematol. 2002; 30(6): 503-12.

Giordano, et al. Distinct transcriptional profiles of adrenocortical tumors uncovered by DNA microarray analysis. Am J Pathol. 2003; 162(2):521-531.

Hagan, A. K., & Zuchner, T. (2011). Lanthanide-based time-resolved luminescence immunoassays. Analytical and bioanalytical chemistry, 400(9), 2847-64.

Hassibi. CMOS Biochips for Point-of-Care Molecular Diagnostics. Hot Chips—Aug. 2014. 32 pgs.

Hassibi, et al. Real-time DNA microarray analysis. Nucleic Acids Res. Nov. 2009;37(20):e132. Epub Aug. 31, 2009.

Held, et al. Modeling of DNA microarray data by using physical properties of hybridization. Proc Natl Acad Sci U S A. Jun. 24, 2003;100(13):7575-80. Epub Jun. 13, 2003.

IDT—Integrated DNA Technologies. Strategies for Attaching Oligonucleotides to Solid Supports. Copyright 2014 (v3). Aug. 10, 2011. 7pages.

"Insulator (eletricity)" from Wikipedia, the free encyclopedia. Printed on Dec. 13, 2018.

Khabzaoui, et al. A multicriteria genetic algorithm to analyze microarray data. In Evolutionary Computation, Jun. 2004. CEC2004. Congress on vol. 2, pp. 1874-1881. IEEE.

Lalkhen, et al. Clinical tests: sensitivity and specificity. Continuing Education in Anaesthesia, Critical Care & Pain. 2008. 8(6), 221-223.

Lee, et al. Seven-color, homogeneous detection of six PCR products. Biotechniques. Aug. 1999;27(2):342-9.

Levine et al. Active CMOS Array for Electrochemical Sensing of Biomolecules, IEEE 2007 Custom Integrated Circuits Conference(CICC), pp. 826-828 (2007).

Li, et al. Bead-Based Melting Analysis In Temperature-Graident Microchannels For Single Nucleotide Polymorphisms Detection. 17th International Conference on Miniaturized Systems for Chemistry and Life Sciences. Oct. 27-31, 2013. Freiburg, Germany. 3 pages.

Liu, et al. TaqMan probe array for quantitative detection of DNA targets. Nucleic Acids Res. 2006; 34(1): e4. Published online Jan. 10, 2006. .

(56) References Cited

OTHER PUBLICATIONS

Manickam, et al. A CMOS Electrochemical Impedance Spectroscopy (EIS) Biosensor Array. IEEE Trans Biomed Circuits Syst. Dec. 2010;4(6):379-90.

Manickam, et al., A Fully Integrated CMOS Fluorescence Biochip for DNA and RNA Testing. IEEE Journal of solid-state circuits, Nov. 2017; 52(11): 2857-2870.

Marcy, et al. Innovative integrated system for real-time measurement of hybridization and melting on standard format microarrays. Biotechniques. Jun. 2008;44(7):913-20.

Matsubara, et al. On-chip nanoliter-volume multiplex TaqMan polymerase chain reaction from a single copy based on counting fluorescence released microchambers. Anal Chem. Nov. 1, 2004;76(21):6434-9.

Metzker, M.L., 2010. Sequencing technologies—the next generation. Nature reviews. Genetics, 11(1), p. 31.

Metzker. Sequencing technologies—the next generation. Nat Rev Genet. Jan. 2010;11(1):31-46. Epub Dec. 8, 2009.

Meuzelaar, et al. DNA diagnostics by surface-bound melt-curve reactions. J Mol Diagn. Feb. 2007;9(1):30-41.

Michael, et al. Randomly Ordered Addressable High-Density Optical Sensor Arrays. Anal. Chem., 1998; 70(7): 1242-1248.

Moore, E.G., Samuel, A.P. and Raymond, K.N., 2009. From antenna to assay: lessons learned in lanthanide luminescence. Accounts of chemical research, 42(4), pp. 542-552.

Murari, K., Etienne-Cummings, R., Thakor, N. and Cauwenberghs, G., 2009. Which photodiode to use: A comparison of CMOS-compatible structures. IEEE sensors journal, 9(7), pp. 752-760.

Namasivayam et al., Advances in on-chip photodetection for applications in miniaturized genetic analysis systems, Journal ofv Micrornechanics and Microengineering vol. 14, issue 1, p. 81-90, Published Aug. 18, 2003.

Pierik, et al. Rapid genotyping of human papillomavirus by post-PCR array-based hybridization techniques. J Clin Microbiol. Apr. 2011;49(4):1395-402. Epub Feb. 16, 2011.

Pont-Kindon, et al. Direct molecular haplotyping by melting curve analysis of hybridization probes: beta 2-adrenergic receptor haplotypes as an example. Nucleic Acids Res. Jun. 3, 2005;33(10):e89.

Pourmand, et al. Direct electrical detection of DNA synthesis. Proc Natl Acad Sci U S A. Apr. 25, 2006;103(17):6466-70. Epub Apr. 13, 2006.

Rant, et al. Switchable DNA interfaces for the highly sensitive detection of label-free DNA targets. Proc Natl Acad Sci U S A. Oct. 30, 2007;104(44):17364-9. Epub Oct. 19, 2007.

Reed, et al. High-resolution DNA melting analysis for simple and efficient molecular diagnostics. Pharmacogenomics. Jun. 2007;8(6):597-608.

Rothe, et al. Multi-target electrochemical biosensing enabled by integrated CMOS electronics. Journal of Micromechanics and Microengineering, 2011, 21(5), 054010.

Sanchez, et al. Linear-after-the-exponential (LATE)-PCR: an advanced method of asymmetric PCR and its uses in quantitative real-time analysis. Proc Natl Acad Sci U S A. Feb. 17, 2004;101(7):1933-8. Epub Feb. 9, 2004.

Schwartz, D.E., Charbon, E. and Shepard, K.L., 2008. A single-photon avalanche diode array for fluorescence lifetime imaging microscopy. IEEE journal of solid-state circuits, 43(11), pp. 2546-2557.

Selvin, P.R., 2002. Principles and biophysical applications of lanthanide-based probes. Annual review of biophysics and biomolecular structure, 31(1), pp. 275-302.

Selvin, P.R., "Lanthanide-Labeled DNA", (2003) Topics in Fluorescence Spectroscopy, vol. 7: DNA Technology, Chapter 6, Kluwer Academic.

Singh, et al. A CMOS-Microfluidic Chemiluminescence Contact Imaging Microsystem. IEEE Journal of Solid-State Circuits. Nov. 2012;47(11) 2822-33.

Singh et al. A Compact Parasitic-Insensitive Dual-Frequency ΔΣ Modulated CMOS Capacitive Architecture, IEEE, pp. 242-245 (2010).

Singh. High Dynamic Range CMOS-Integrated Biosensors. https://repositories.lib.utexas.edu/bitstream/handle/2152/29144/SINGH-DISSERTATION-2013.pdf?sequence=1. May 1, 2013. Accessed on Feb. 11, 2016. 189 pages.

Soon, et al. High Throughput Melting Curve Analysis In Monolithic Silicon-Based Microfluidic Device. 14th International Conference on Miniaturized Systems for Chemistry and Life Sciences. Oct. 3-7, 2010. Groningen, The Netherlands.

Sosnowski. A chip-based genetic detector for rapid identification of individuals. Document No. 213911. Award No. 1997-LB-XV-0004. Apr. 2006. 100 pages.

Stochastic Matrix, one page, 2013. Wolfram MathWorld. Obtained online on May 29, 2013.

Tang, et al. Simple and effective method for generating single-stranded DNA targets and probes. Biotechniques. Jun. 2006;40(6):759-63.

Temiz et al. Robust Microelectrodes Developed for Improved Stability in Electrochemical Characterization of Biomolecular Layers, IEEE Sensors 2010 Conference, pp. 1051-1055 (2010).

Tokuda et al., A CMOS image sensor with optical and potential dual imaging function for on-chip bioscientific applications, Sensors and Actuators A: Physical, vol. 125, Issue 2, Jan. 10, 2006, pp. 273-280.

Tomlinson, et al. Influence of the length of target DNA overhang proximal to the array surface on discrimination of single-base mismatches on a 25-mer oligonucleotide array. BMC Res Notes. Apr. 17, 2014;7:251.

Vikalo, et al. A statistical model for microarrays, optimal estimation algorithms, and limits of performance. Signal Processing, IEEE Transactions on, 2006, 54(6), 2444-2455.

Vikalo, et al. Optimal estimation of gene expression levels in microarrays. Presented at the IEEE Int. Workshop Genomic Signal Processing Statistics, Newport, RI, May 22-24, 2005.

Vikalo, et al. Proof of publication date of [Vikalo, et al. Optimal estimation of gene expression in microarrays.] as Mar. 5, 2005, one page, acquired from USPTO Library on Jun. 13, 2014.

Wilhelm, et al., Real-time polymerase chain reaction. Chembiochem, 2003;4:1120-1128.

Yuan, J. and Wang, G., 2006. Lanthanide-based luminescence probes and time-resolved luminescence bioassays. TrAC Trends in Analytical Chemistry, 25(5), pp. 490-500.

Yuen, et al. Accuracy and calibration of commercial oligonucleotide and custom cDNA microarrays. Nucleic Acids Res. May 15, 2002;30(10):e48.

Zhang. Noisy Data with Outliers, one page, 1996. Obtained online on Feb. 9, 2013.

Zhu, et al. Multiplex asymmetric PCR-based oligonucleotide microarray for detection of drug resistance genes containing single mutations in Enterobacteriaceae. Antimicrob Agents Chemother. Oct. 2007;51(10):3707-13. Epub Jul. 23, 2007.

A. Agah, et al., A High-Resolution Low-Power Incremental Lb. ADC With Extended Range for Biosensor Arrays, IEEE Journal of Solid-State Circuits, vol. 45, No. 6, pp. 1099-1110 (2010) (Year: 2010).

Ansevin, et al. High-resolution thermal denaturation of DNA. I. Theoretical and practical considerations for the resolution of thermal subtransitions. Biopolymers. Jan. 1976;15(1):153-74.

Ausubel, et al. Current Protocols in Molecular Biology. Greene Publishing Associates and Wiley-Interscience. John Wiley & Sons. New York. 1987. (Table of Contents).

Beaucage, et al. The functionalization of oligonucleotides via phosphoramidite derivative. Tetrahedron. 1993;49(10):1925-63.

Brill et al. Synthesis of oligodeoxynucleoside phosphorodithioates via thioamidites. J. Am. Chem. Soc. 111:2321-2322 (1989).

C. Y. Huang, Design of a voltammetry potentiostat for biochemical sensors, Analog Integr. Cir. Sig. Process, vol. 67, pp. 375-381 (2011) (Year: 2011).

Campbell, et al. Large-scale approaches for glycobiology. Genome Biology. 2005; 6(11):236.1-8.

Carlsson et al. Screening for genetic mutations. Nature 380(6571):207 (1996).

Clegg. Fluorescence resonance energy transfer and nucleic acids. Methods Enzymol. 1992;211:353-88.

(56) References Cited

OTHER PUBLICATIONS

Co-pending U.S. Appl. No. 16/670,126, inventors Hassibiarjang et al., filed Oct. 31, 2019.
Co-pending U.S. Appl. No. 16/777,051, inventors Hassibiarjang et al., filed Jan. 30, 2020.
De Mesmaeker et al. Comparison of Rigid and Flexible Backbones in Antisense Oligonucleotides Bioorg Med Chem Lett 4(3):395-398 (1994).
Dempcy et al. Synthesis of a thymidyl pentamer of deoxyribonucleic guanidine and binding studies with DNA homopolynucleotides PNAS USa 92:6097-6101 (1995).
Diehl et al. BEAMing: single-molecule PCR on microparticles in water-in-oil emulsions. Nature Methods 3(7):551-559 (2006).
Dowling, et al. Exponential parameter estimation in the presence of known components and noise. Antennas and Propagation, IEEE Trans. On Antennas and Propag, 1994, 42(5), 590-599.
Eckstein. Oligonucleotides and Analogues: A Practical Approach. Press at Oxford University Press, 1991: 313.
Eltoukhy, et al. A 0.18-um CMOS bioluminescence detection lab-on-chip. Solid-State Circuits, IEEE Journal of: Mar. 2006; 41(3):651-662.
Falconnet, et al. Rapid, sensitive and real-time multiplexing platform for the analysis of protein and nucleic-acid biomarkers. Anal Chem. Feb. 3, 2015;87(3):1582-9. Epub Jan. 21, 2015.
Feng, L. Probing lipid-protein interactions using lipid microarrays. Prostaglandins Other Lipid Mediat. 2005; 77(1-4):158-67.
Forster. Experimentelle und theoretische Untersuchung des zwischenmolekularen Übergangs von Elektronenanregungsenergie. Zeitschrift für naturforschung A 4.5 1949: 321-327.
Foss et al. Effects of fixative and fixation time on the extraction and polymerase chain reaction amplification of RNA from paraffin-embedded tissue. Comparison of two housekeeping gene mRNA controls. Diagn Mol Path 3:148-155 (1994).
Gao et al. Unusual conformation of a 3'-thioformacetal linkage in a DNA duplex. J. Biomolecular NMR.34:17-34 (1994).
Guatelli et al. Isothermal, in vitro amplification of nucleic acids by a multienzyme reaction modeled after retroviral replication. PNAS USA 87(5):1874-1878 (1990).
Gunderson, et al.—Decoding Randomly Ordered DNA Arrays. Genome Res. 14:870-877, 2004.
Hall. Biosensors. Prentice-Hall. Englewood Cliffs, NJ. 1991. (Table of Contents only).
Han, et al., Quantum-dot-tagged microbeads for multiplexed optical coding of biomolecules. Nature Biotechnology 19.99 (Jul. 2001): 631-635.
Hassibi, et al. A probabilistic model for inherent noise and systematic errors of microarrays. Proc of Workshop on Genomics Signal Processing and Statistics. 2005: 1-2.
Hassibi, et al. A Programmable 0.18-um CMOS Electrochemical Sensor Microarray for Biomolecular Detection. Sensors Journal, IEEE,Dec. 2006. vol. 6, Issue: 6: 1380-1388.
Hassibi, et al. A stochastic model and simulation algorithm for polymerase chain reaction (PCR) systems. Proc of Workshop on Genomics Signal Processing and Statistics. 2004: 1-4.
Hassibi, et al. Biological shot-noise and quantum-limited signal-to-noise ratio in affinity-based biosensors. J Appl Phys. 2005; 97: 084701.1-10.
Hassibi, et al. Effects of Scaling on the SNR and Speed of Biosensors. Engineering in Medicine and Biology Society, 2004. IEMBS'04. 26th Annual International Conference of the IEEE. vol. 1. IEEE, 2004.
Hassibi, et al. On noise processes and limits of performance in biosensors.J. Appl. Phys. 102, 014909 (2007) (12 pages).
Hassibi. Integrated Microarrays. Ph.D. Thesis Stanford University, 2005 (142 pgs)..
Held, et al. Relationship between gene expression and observed intensities in DNA microarrays—a modeling study. Nucleic Acids Res. May 24, 2006;34(9):e70.

Horn et al. Oligonucleotides with alternating anionic and cationic phosphoramidate linkages: Synthesis and hybridization of stereo-uniform isomers. Tetrahedron Lett 37:743-746 (1996).
Howell, et al. iFRET: an improved fluorescence system for DNA-melting analysis. Genome Res. Sep. 2002;12(9):1401-7.
Jenkins et al. The Biosynthesis of Carbocyclic Nucleosides Chem Soc Re 24:169-176 (1995).
Jepsen, et al. Locked nucleic acid: a potent nucleic acid analog in therapeutics and biotechnology. Oligonucleotides. 2004;14(2):130-46.
Kiedrowski, et al. Parabolic growth of a self-replicating hexadeoxynucleotide bearing a 3'-5'-phosphoamidate linkage. Angew. Chem. Intl. Ed. English 1991;30:423-426.
Lai et al. PrimRglo: A multiplexable quantitative real-time polymerase chain reaction system for nucleic acid detection. Analytical Biochemistry 422:89-95 (2012).
Landegren. Molecular mechanics of nucleic acid sequence amplification. Trends in Genetics, 1993, 9(6), 199-204.
Lee, et al. Nucleic acid amplification technologies: Application to disease diagnosis. Springer Science & Business Media, 1997.
Letsinger et al. Cationic Oligonucleotides J Am Chem Soc 110:4470-4471 (1988).
Letsinger, et al. Hybridization of alternating cationic/anionic oligonucleotides to RNA segments. Nucleosides, Nucleotides & Nucleic Acids 13.6-7 (1994): 1597-1605.
Lipsky, et al. DNA melting analysis for detection of single nucleotide polymorphisms. Clin Chem. Apr. 2001;47(4):635-44.
Liu, et al., Biosensing based upon molecular confinement in metallic nanocavity arrays. Proceedins of SPIE 5703. Plasmonics in biology and medicine II, Mar. 31, 2005, pp. 99-106.
Lizardi, et al. Exponential amplification of recombinant-RNA hybridization probes. Nature Biotechnology 6.10 (1988): 1197-1202.
Lockhart, et al. Multiplex metallica. Nat Biotechnol. Dec. 2001;19(12):1122-3.
Lund-Olesen, et al., Sensitive on-chip quantitative real-time PCR performed on an adaptable and robust platform. Biomed Microdevices. Dec. 2008;10(6):769-776. doi: 10.1007/s10544-008-9189-0.
M. Stanacevic, VLSI Potentiostat Array with Oversampling Gain Modulation for Wide-Range Neurotransmitter Sensing IEEE Transactions on Biomedical Circuits and Systems, vol. 1, No. 1, pp. 63-72 (2007) (Year: 2007).
Margulies, et al. Genome sequencing in microfabricated high-density picolitre reactors. Nature. Sep. 15, 2005;437(7057):376-80. Epub Jul. 31, 2005.
Merrifield, R. B., "Solid-Phase Peptide Synthesis. III. An Improved Synthesis of Bradykinin," Biochemistry, vol. 3, 9, pp. 1385-1390, Sep. 1964.
Nanogen. A chip-based genetic detector for rapid identification of individuals. National institute of justice—Project No. 97-LB-VX-0004. Apr. 2006. 102 pgs.
Notice of allowance dated Sep. 23, 2013 for U.S. Appl. No. 11/844,996.
Novak, et al., An integrated fluorescence detection system for lab-on-a-chip applications. Lab on a chip, royal society of chemistry. Nov. 2006; 7(1):27-29.
P. M. Levine, et al., Active CMOS Sensor Array for Electrochemical Biomolecular Detection, IEEE Journal of Solid-State Circuits, vol. 43, No. 8, pp. 1859-1871 (2008) (Year: 2009).
Parikh, et al. A CMOS Image Sensor for DNA Microarray, IEEE Custom Integrated Circuit Conf., 2007 26: 821-824.
Paska et al. Effect of formalin, acetone, and RNAlater fixatives on tissue preservation and different size amplicons by real-time PCR from paraffin-embedded tissue. Diagn Mol Path 13(4):234-240 (2004).
PCT/US2020/022830 International Search Report and Written Opinion dated Jul. 30, 2020.
Petersson, et al. A review of the parameter estimation problem of fitting positive exponential sums to empirical data. Technical Report IMa-TOM-1997-08; Available from Applied Mathematics and Computation. Feb. 2002. vol. 126: No. 1. 31-61.
Rehmna, et al. Immobilization of acrylamide-modified oligonucleotides by co-polymerization. Nucleic Acids Res. Jan. 15, 1999;27(2):649-55.

(56) References Cited

OTHER PUBLICATIONS

Reverter, et al. A rapid method for computationally inferring transcriptome coverage and microarray sensitivity. Bioinformatics. Jan. 1, 2005;21(1):80-9. Epub Aug. 12, 2004.
Ririe, et al. Product differentiation by analysis of DNA melting curves during the polymerase chain reaction. Anal Biochem. Feb. 15, 1997;245(2):154-60.
Rothberg, et al. An integrated semiconductor device enabling non-optical genome sequencing. Nature. Jul. 20, 2011;475(7356):348-52. .
Rothberg et al., "The Development and Impact of 454 Sequencing," Nature Biotechnology, vol. 26, No. 10, pp. 1117-1124, Oct. 9, 2008.
S. Hwang, et al., CMOS Microelectrode Array for Electrochemical Lab-on-a-Chip Applications, IEEE Sensors Journal, vol. 9, No. 6, pp. 609-615 (2009) (Year: 2009).
Sakurai et al., "Real-Time Monitoring of DNA Polymerase Reactions by a Micro ISFET pH Sensor," Anal. Chem., 64, No. 17, pp. 1996-1997, Sep. 1, 1992.
Salm, et al. Ultralocalized thermal reactions in subnanoliter droplets-in-air. Proc Natl Acad Sci U S A. Feb. 26, 2013;110(9):3310-5. .
Sambrook, et al. Molecular cloning: A Laboratory Manual. 2nd Edition. 1989. New York: Cold spring harbor laboratory press.
Sanghvi, et al. Chapters 6 and 7, ASC Symposium Series 580, "Carbohydrate Modifications in Antisense Research", 1994.
Sanghvi, et al. ed. Chapters 2 and 3, ASC Symposium Series 580—Carbohydrates Modifications in Antisense Research. American Chemical Society. Washington, DC. 1994.
Savyon Diagnostics. Nano CHIP. www.nanochip400.com. NG Jun. 2010—VER1. 8pgs.
Schena, et al. Quantitative monitoring of gene expression patterns with a complementary DNA microarray. Science. Oct. 20, 1995;270(5235):467-70.
Schena. Microarray Analysis. Wiley-Liss: A John Wiley & Sons, Inc., Publication. 2003. Hoboken, New Jersey. (Table of contents only).
Scherf, et al. Letter from Uwe Scherf-S to Kristen Kanack re: K143178 Section 510(k). Department of Health & Human Services. Jan. 30, 2015. 9pgs.
Schienle, et al. A fully electronic DNA sensor with 128 positions and in-pixel A/D conversion. IEEE Journal of vol. 39, Issue 12, Dec. 2004 pp. 2438-2445.
Singh, et al., CMOS biochips for hypothesis-driven DNA analysis. IEEE Biomedical circuits and systems conference. Oct. 2014.
Stillman, et al. FAST slides: a novel surface for microarrays. Biotechniques. Sep. 2000;29(3):630-5.
Stimpson, et al. Real-time detection of DNA hybridization and melting on oligonucleotide arrays by using optical wave guides. Proc Natl Acad Sci U S A. Jul. 3, 1995;92(14):6379-83.
Stolovitzky, et al. Efficiency of DNA replication in the polymerase chain reaction. Proc Natl Acad Sci USA. 1996; 93: 12947-52.
Stoughton. Applications of DNA microarrays in biology. Annu Rev Biochem. 2005;74:53-82.
Tao, et al., Blocking oligo—a novel approach for improving chip-based DNA hybridization efficiency. Mol Cell Probes. Aug. 2003;17(4):197-202.
Tijssen, P. Ch 2—Overview of principles of hybridization and the strategy of nucleic acid probe assays. Laboratory Techniques in Biochemistry and Molecular Biology: Hybridization with Nucleic Acid Probes. Elsevier Science Publisher, Netherlands. 1993. vol. 24; 19-78 Pages.
Tijssen. Chapter 3 of Laboratory Techniques in Biochemistry and Molecular Biology: Hybridization with Nucleic Acid Probes, Part I. Theory and Nucleic Acid Preparation. Elsevier, N.Y. 1993.
Tolley, et al. Single-chain polymorphism analysis in long QT syndrome using planar waveguide fluorescent biosensors. Anal Biochem. Apr. 15, 2003;315(2):223-37.
Tsuji et al. Development of a Time-Resolved Fluorometric Method for Observing Hybridization in Living Cells Using Fluorescence Resonance Energy Transfer. Biophysical Journal, Jul. 2001, 81:501-515.
Tu, et al. Quantitative noise analysis for gene expression microarray experiments. Proc Natl Acad Sci U S A. Oct. 29, 2002;99(22):14031-6. Epub Oct. 18, 2002.
Van Der Veen, et al. Subspace-based signal analysis using singular value decomposition. Proceedings of the IEEE, 1993, 81(9), 1277-1308.
Walczak, et al., Miniaturized System for Real-Time PCR in Low-Cost Disposable LTCC Chip With Integrated Optical Waveguide. 12th international conference on miniaturized systems for chemistry and life sciences. 2008; 1078-1080.
Wang, et al. Estimation of the mutation rate during error-prone polymerase chain reaction. J Comput Biol. 2000; 7(1-2): 143-58.
Wittwer, et al. Continuous fluorescence monitoring of rapid cycle DNA amplification. Biotechniques. Jan. 1997;22(1):130-8.
You, et al., Measuring thermodynamic details of DNA hybridization using fluorescence, Biopolymers, vol. 95, 2011; pp. 472-486.
Zhu, et al. Protein chip technology. Current Opinion in Chemical Biology. 2003; 7: 55-63.

* cited by examiner

METHODS AND SYSTEMS FOR TIME-GATED FLUORESCENT-BASED DETECTION

CROSS-REFERENCE

This application is a continuation of International Application No. PCT/US2020/022830, filed Mar. 13, 2020, which claims the benefit of U.S. Provisional Patent Application No. 62/818,614, filed on Mar. 14, 2019, each of which is entirely incorporated herein by reference.

BACKGROUND

Continuous wave (CW) fluorescence-based spectroscopy, adopted into both heterogeneous and homogenous biochemical assays, may be used in life science research as well as in-vitro diagnostics. End-point fluorescence-based detection methods for example, may be widely applied for detecting and/or monitoring capturing probe and analyte bindings in surface-based (solid-phase) biochemical assays. Generally, the analyte may contain a fluorophore construct, which may emit light when excited by an optical excitation source. The emission may occur at a longer wavelength than the excitation source. When the capturing probe is attached to a specific and/or addressable coordinate on the surface, analyte capturing may result in the generation of localized fluorescence signals; a phenomenon that can be detected by optical detection devices. Example optical detection devices may include charge-coupled device (CCD) or complementary metal-oxide semiconductor (CMOS) cameras.

Time-gated fluorescence (TGF) analysis is a variant of fluorescence spectroscopy that may be used in certain biochemical assays. Unlike CW fluorescence methods, in TGF, the excitation light may not be continuous and may be applied in a fraction of time only, i.e., it may be time-gated.

SUMMARY

In TGF, responses of the analytes to a series of finite time optical excitation pulses are analyzed after each excitation pulse is turned off. In conventional TGF, the emitted photon flux from fluorophores may be measured after every individual excitation pulse. One way to measure the photon flux is to quantify the photo-induced charge within specific integration time interval of a detector (FIG. 1). Such measured signals, when combined with fluorophore labelling of capture probes and/or analytes, can then be used to evaluate a presence, abundance, and occasionally the characteristics of the target analytes.

In certain applications, TGF may have advantages over CW fluorescence. For example, TGF may offer a much higher signal-to background when fluorophore copy number is relatively low. With a sufficiently fast optical excitation switching source, there may be almost no background from the excitation signal during detection. Furthermore, if fluorophores with long life time are used (e.g., Lanthanide chelates), one can also eliminate short lived auto-fluorescence background emissions from surrounding materials and/or biomolecular structures. Examples of auto-fluorescence sources may include plastics, organic polymers, or intercellular debris.

While TGF may be advantageous, its practical implementation can be quite challenging. The first set of challenges may be related to the speed in which the pulsed excitation and detection may occur. In conventional TGF configurations, optical and electronics systems with pulse frequency >100 MHz may be needed. The second set of challenges may originate from the inherent low number of photons that are emitted after each excitation pulse, with a total count less than or equal to the number of fluorophores. Finally, TGF may offer limited "multi-color" capabilities compared to CW fluorescence. In TGF, differentiating fluorophores based on their life-time may require higher speed and lower noise performance for the optics and electronics.

In the present disclosure, apparatus and methods to create high-performance, highly-integrated, and cost-efficient TGF system using semiconductor biochip devices and technologies have been provided. The methods and apparatus of the present disclosure may be used in life science and molecular diagnostics in Genomics and Proteomics, particularly massively-parallel DNA and protein analysis and DNA sequencing.

An aspect of the present disclosure provides a device for detecting a presence or absence of an analyte in a solution, comprising: a chip comprising a sensor comprising an electronic shutter, wherein the sensor is configured to (i) collect a signal from the solution generated upon exposure of the solution to an excitation pulse within a first time period, (ii) with aid of the electronic shutter, remove photo-induced charge generated within a second time period in the sensor by the excitation pulse, wherein the second time period is different from the first time period, and (iii) subsequent to the photo-induced charge being removed, generate an output signal derived at least in part from the signal, wherein the output signal is indicative of the presence or absence of the analyte.

In some embodiments, the second time period precedes the first time period. In some embodiments, the second time period is greater than duration of the excitation pulse. In some embodiments, the chip comprises a plurality of individually addressable locations, wherein the sensor comprising the electronic shutter is disposed on a first location of the plurality of individually addressable locations; and wherein an additional sensor comprising an additional electronic shutter is disposed on an additional location of the plurality of individually addressable locations.

In some embodiments, the signal comprises an electrical signal, and wherein the sensor further comprises at least one transducer configured to convert an optical signal from the solution to the electrical signal. In some embodiments, the electronic shutter comprises an electronic shutter switch operably coupled to the at least one transducer, which electronic shutter switch is configured to facilitate the removal of the photo-induced charge from the at least one transducer upon application of a voltage to the electronic shutter switch. In some embodiments, the sensor further comprises at least one integrator configured to integrate the electrical signal. In some embodiments, the sensor further comprises at least one integration switch disposed between and operably coupled to the at least one transducer and the at least one integrator, wherein the at least one integration switch is configured to transfer the electrical signal from the at least one transducer to the at least one integrator. In some embodiments, the sensor further comprises at least one additional transducer operably coupled to the at least one integrator, which the at least one additional transducer is configured to convert the electrical signal integrated by the at least one integrator to the output signal. In some embodiments, the signal comprises photo-induced charge, and wherein the output signal comprises voltage. In some embodiments, the chip is included in a complementary metal oxide semiconductor (CMOS) integrated circuit (IC).

In some embodiments, the chip further comprises a biosensing layer adjacent to the sensor, and the biosensing layer comprises at least one probe that specifically binds to the analyte. In some embodiments, the signal is derived at least in part from an optical signal produced by a label associated with the analyte upon binding of the analyte to the at least one probe. In some embodiments, the label is a fluorophore. In some embodiments, the signal is derived at least in part from an optical signal or change thereof from the at least one probe or the analyte upon binding of the analyte to the at least one probe. In some embodiments, the at least one probe comprises an energy donor and the analyte comprises an energy acceptor. In some embodiments, the energy donor is a fluorophore, and wherein the energy acceptor is an additional fluorophore or a quencher. In some embodiments, the biosensing layer comprises at least one control probe, and wherein the sensor is configured to collect a control signal from the at least one control probe and normalize the collected signal using the control signal. In some embodiments, the at least one control probe does not bind to or interact with the analyte. In some embodiments, the device further comprises a reaction chamber, a controllable fluidic unit, a temperature control unit, and a digital unit. In some embodiments, the reaction chamber is configured to interface the solution with the chip, and wherein the interfacing comprises an interaction between the analyte and the biosensing layer of the chip. In some embodiments, the controllable fluidic unit is configured to transfer at least a portion of the solution into or out of the reaction chamber. In some embodiments, the digital unit is configured to receive or store the output signal from the chip. In some embodiments, the chip is configured to repeat (i)-(ii) multiple times prior to (iii). In some embodiments, the output signal is a single output.

An aspect of the present disclosure provides a method for detecting a presence or absence of an analyte in a solution, comprising:

(a) activating a chip comprising a sensor comprising an electronic shutter, wherein the sensor is configured to (i) collect a signal generated upon exposure of the solution to an excitation pulse within a first time period, (ii) with aid of the electronic shutter, remove photo-induced charge generated within a second time period in the sensor by the excitation pulse, wherein the second time period is different from the first time period, and (iii) subsequent to the photo-induced charge being removed, generate an output signal derived at least in part from the signal, wherein the output signal is indicative of the presence or absence of the analyte;

(b) removing the photo-induced charge generated within the second time period in the sensor by the excitation pulse, with aid of the electronic shutter;

(c) collecting the signal generated upon exposure of the solution to the excitation pulse within the first time period; and (d) subsequent to the photo-induced charge being removed, generating the output signal derived at least in part from the signal, which output signal is indicative of the presence or absence of the analyte.

In some embodiments, the sensor is a time-gated fluorescence (TGF) photo sensor. In some embodiments, the method further comprises integrating the signal collected in (c) using the sensor. In some embodiments, the method further comprises, repeating (b)-(c) one or more times. In some embodiments, the one or more times comprise greater than or equal to about 100 times.

Another aspect of the present disclosure provides a device for detecting a signal, comprising: a chip comprising a sensor and an electronic shutter, wherein the sensor is configured to (i) detect the signal within a given time period, and (ii) yield data indicative of a charge generated by the signal, and wherein the electronic shutter is configured to remove a photo-induced charge which comprises a charge generated by an excitation pulse within a time period prior to the given time period; and a readout circuitry operatively coupled to the sensor, wherein the readout circuitry is configured to transmit the data from the sensor to memory.

In some embodiments, the readout circuitry is part of the chip. In some embodiments, the memory is external to the readout circuitry. In some embodiments, the signal is a fluorescence signal. In some embodiments, the chip comprises a sensor array comprising a plurality of individually addressable locations; the sensor and the electronic shutter is disposed on a first location of the plurality of individually addressable locations; and a second sensor and a second electronic shutter is disposed on a second location of the plurality of individually addressable locations. In some embodiments, the sensor is further configured to integrate the charge generated by the signal. In some embodiments, the sensor comprises an integration switch. In some embodiments, the sensor comprises at least one photo-to-charge transducer and at least one charge integrator, and the at least one integration switch locates between the at least one photo-to-charge transducer and the at least one charge integrator. In some embodiments, the chip is included in a complementary metal oxide semiconductor (CMOS) integrated circuit (IC). In some embodiments, the CMOS IC further comprises a heater and temperature control system. In some embodiments, the heater and temperature control system controls temperature at the plurality of individually addressable locations.

In some embodiments, the chip further comprises a biosensing layer adjacent to the sensor, and the biosensing layer comprises a surface comprising a plurality of probes. In some embodiments, probes of the plurality of probes are identical. In some embodiments, the sensor receives a fluorescent light from a fluorescent source associated with the biosensing layer. In some embodiments, the fluorescent source is a fluorophore. In some embodiments, the fluorophore is attached to at least one probe of the plurality of probes. In some embodiments, the plurality of probes comprise at least one control probe. In some embodiments, the at least one control probe does not bind to or interact with a target molecule. In some embodiments, each probe of the plurality of probes specifically binds to or interacts with a target molecule. In some embodiments the target molecule comprises a target molecular label. In some embodiments, the target molecular label comprises a target fluorophore. In some embodiments, each probe of the plurality of probes further comprises a molecular label. In some embodiments, the molecular label comprises a fluorophore. In some embodiments, the specific binding or interaction between the probe and the target molecule changes the fluorescence emitted from the fluorophore. In some embodiments, the device further comprises a reaction chamber, a controllable fluidic system, a temperature control system, and a digital system. In some embodiments, the reaction chamber interfaces a sample with the biochip, and the interfacing comprises an interaction between the sample and the biosensing layer of the chip. In some embodiments, the controllable fluidic system transfers at least one reagent into and/or out of the reaction chamber. In some embodiments, the at least one reagent comprises the sample. In some embodiments, the temperature control system sets a first temperature at the reaction chamber at a first time point. In some embodiments, the digital system sends instructions to the chip and the temperature control system. In some embodiments, the digital system further stores the data from the chip. In some embodiments, the digital system further receives the data from the chip.

Still another aspect of the present disclosure provides a method for detecting a signal, comprising activating a chip comprising a sensor and an electronic shutter, wherein the sensor is configured to (i) detect the signal within a given time period, and (ii) yield data indicative of a charge generated by the signal, and wherein the electronic shutter is configured to remove a photo-induced charge which comprises a charge generated by an excitation pulse within a time period prior to the given time period; (b) using the electronic shutter to remove the photo-induced charge within the time period prior to the given time period; (c) using the sensor to detect the signal within the given time period and yield the data indicative of the charge generated by the signal; and (d) transmitting the data to memory.

In some embodiments, the sensor is a time-gated fluorescence (TGF) photo sensor. In some embodiments, (c) further comprises integrating the charge generated by the signal using the sensor. In some embodiments, the method further comprises, repeating (a)-(c) one or more times. In some embodiments, the one or more times comprise greater than or equal to about 10 times. In some embodiments, the one or more times comprise greater than or equal to about 50 times. In some embodiments, the one or more times comprise greater than or equal to about 100 times. In some embodiments, the method further comprises generating an output signal using the chip. In some embodiments, the output signal is a single output signal. In some embodiments, the chip comprises a plurality of independently addressable locations. In some embodiments, the chip further comprises an additional sensor and an additional electronic shutter, the sensor and the electronic shutter are disposed on a first location of the plurality of independently addressable locations, and the additional sensor and the additional electronic shutter are disposed on a second location of the independently addressable locations. In some embodiments, the first location is different from the second location. In some embodiments, the method further comprises using the additional electronic shutter to remove an additional photo-induced charge within the time period prior to the given time period. In some embodiments, the method further comprises using the additional sensor to detect an additional charge generated by an additional signal within the given time period and yield additional data indicative of the additional charge generated by the additional signal. In some embodiments, the method further comprises integrating the additional charge using the sensor. In some embodiments, the plurality of independently addressable locations comprises greater than or equal to about 100 locations. In some embodiments, the plurality of independently addressable locations comprises greater than or equal to about 1,000 locations. In some embodiments, the plurality of independently addressable locations comprises greater than or equal to about 100,000 locations. In some embodiments, the plurality of independently addressable locations comprises greater than or equal to about 100 locations are pixels.

Another aspect of the present disclosure provides a method for operating a time-gated fluorescence (TGF) detection, comprising (a) activating a chip comprising a surface and an integrated circuit (IC) comprising at least one photo-sensor, wherein the IC comprises an electronic shutter; (b) directing a pulse of excitation light from an excitation light source to the surface; (c) during a first time period, using the electronic shutter to remove a first photo-induced charge from the photo-sensor, wherein the first photo-induced charge comprises a charge generated by the pulse of excitation light during the first time period; (d) during a second time period subsequent to the first time period, measuring a second photo-induced charge generated in the photo-sensor, wherein the surface is not exposed to the excitation pulse during the second time period; and (e) integrating the second photo-induced charge measured in (d) during the second time period.

In some embodiments, the excitation pulse is generated by a laser. In some embodiments, the integrating is conducted by using a sub-circuit comprised in the chip. In some embodiments, the method further comprises, repeating (a)-(e) one or more times. In some embodiments, the one or more times comprise greater than or equal to about 10 times. In some embodiments, the one or more times comprise greater than or equal to about 50 times. In some embodiments, the one or more times comprise greater than or equal to about 100 times. In some embodiments, the method further comprises generating an output signal. In some embodiments, the output signal is a single output. In some embodiments, the method further comprises resetting once the sub-circuit. In some embodiments, the sub-circuit is not reset during the repeating. In some embodiments, the sub-circuit is not reset between each of the repeating. In some embodiments, the method further comprises, prior to (b), resetting the sub-circuit. In some embodiments, there is a gap between the first time period and the second time period. In some embodiments, the surface comprises a biosensing layer comprising at least one probe. In some embodiments, the at least one probe comprises a fluorophore. In some embodiments, the fluorophore emits a fluorescent signal when excited by the excitation light. In some embodiments, the surface comprises a target molecule. In some embodiments, the at least one target molecule comprises a fluorophore. In some embodiments, the fluorophore emits a fluorescent signal when excited by the excitation light. In some embodiments, the at least one probe specifically binds to or interacts with the target molecule, thereby modulating the fluorescent signal emitted from the fluorophore comprised in the at least one probe. In some embodiments, the integrating comprises integrating photocurrent. In some embodiments, the method further comprises converting the integrated photocurrent from an analog format to a digital format.

Another aspect of the present disclosure provides a device comprising: a chip operatively coupled to a light source, the chip comprising a sensor which is configured to: (a) periodically detect one or more signals from an analyte associated with a surface of the chip, wherein the one or more signals are produced during or subsequent to subjecting the analyte to the light source; (b) integrate at least a subset of the one or more signals detected in (a) to produce an integrated signal; and (c) generate an output signal based on the integrated signal.

In some embodiments, the chip comprises an integrated complementary metal-oxide semiconductor (CMOS) chip. In some embodiments, the output signal is a single output signal. In some embodiments, the sensor is a time-gated fluorescence (TGF) sensor. In some embodiments, the device does not comprise an optical filter disposed adjacent to the chip. In some embodiments, the output signal is indicative of a characteristic of the analyte. In some embodiments, the chip comprises a sensor array comprising a plurality of sensors. In some embodiments, each of the plurality of sensors is disposed at an individually addressable location of the sensor array. In some embodiments, the analyte comprises a fluorophore. In some embodiments, the output signal is used to measure a lifetime of the fluorophore. In some embodiments, the analyte is immobilized on the surface. In some embodiments, the analyte is part of a molecule immobilized on the surface. In some embodiments, the analyte is immobilized on the surface via a linker. In some embodiments, the one or more signals comprise fluorescent photons. In some embodiments, the sensor comprises a transducer configured to convert the fluorescence photons into an electrical signal. In some embodiments, the sensor comprises a transducer configured to convert the fluorescence photons into charges. In some embodiments, the sensor further comprises an integrator configured to integrated the one or more signals. In some embodiments, the sensor comprises a switch operatively coupled to the transducer and the integrator. In some embodiments, the switch transfers the charges from the transducer to the integrator. In some embodiments, the integrator is operatively coupled to an additional transducer. In some embodiments, the additional transducer converts the charges to an electrical signal, thereby generating the output signal comprising the electrical signal. In some embodiments, the electrical signal comprises a voltage. In some embodiments, the light source is a pulsed light source. In some embodiments, the pulsed light source is a laser, or a light emitting diode. In some embodiments, the pulsed light source is periodically modulated in a predetermined frequency.

Another aspect of the present disclosure provides a method comprising: (a) activating a chip comprising a sensor which is configured to (i) periodically detect one or more signals from an analyte associated with a surface of the chip, wherein the one or more signals are produced during or subsequent to subjecting the analyte to a light source; (ii) integrate at least a subset of the one or more signals detected in (i) to produce an integrated signal; and (iii) generate an output signal based on the integrated signal; (b) directing the light source to the chip to generate the one or more signals; (c) detecting periodically the one or more signals from the analyte during or subsequent to subjecting the analyte to the light source; (d) integrating the at least the subset of the one or more signals to produce the integrated signal; and (e) generating an output signal based on the integrated signal.

In some embodiments, the light source is a pulsed light source. In some embodiments, (c) is conducted periodically at given intervals. In some embodiments, (c) occurs during or after each time the pulsed light source is off. In some embodiments, the output signal is a single output signal. In some embodiments, (d) is conducted using an integrator. In some embodiments, (c) or (e) is conducted using a transducer. In some embodiments, the output signal is an electrical signal. In some embodiments, the one or more signals are detected by the sensor in the absence of passing through an optical filter.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

DETAILED DESCRIPTION

Figure 1:
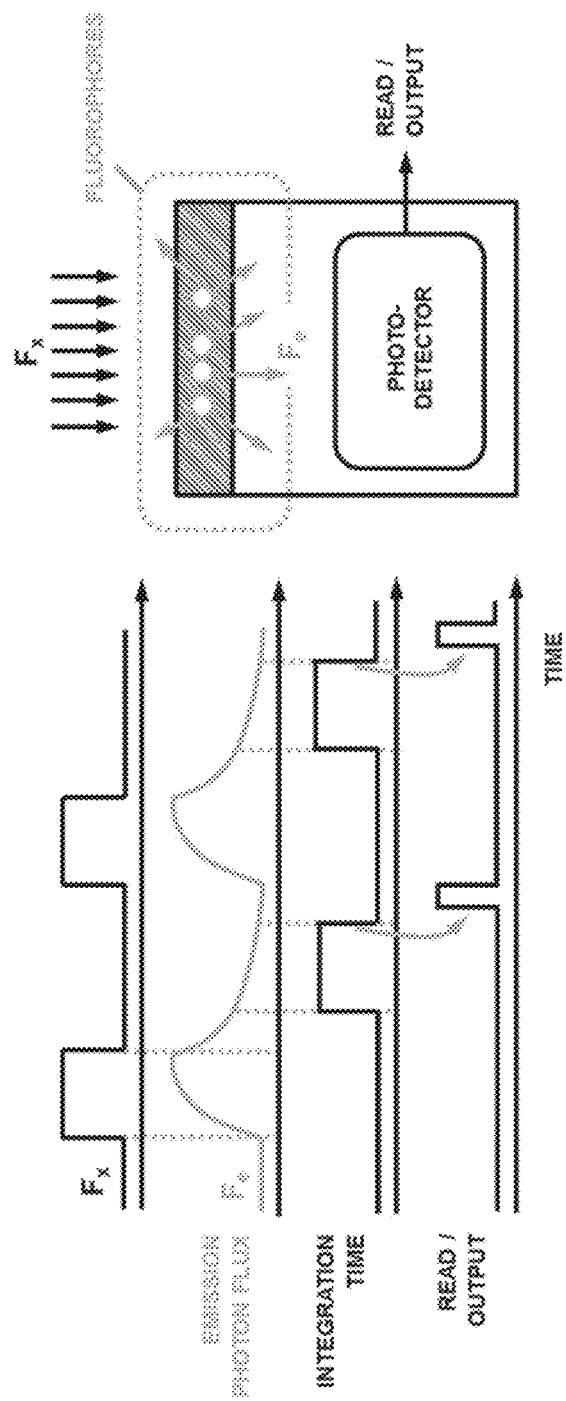
FIG. 1 illustrates a timing diagram and waveforms of an example time-gated fluorescence detection.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "analyte" or "target" as used herein generally refers to a molecular species to be detected. Examples include small molecules such as organic compounds, drugs, hormones, lipids, steroids, or metabolites; polynucleotides such as deoxyribonucleic acid (DNA) molecules, ribonucleic acid (RNA) molecules, and peptide nucleic acid (PNA); polypeptides such as proteins, peptides, antibodies, antigens, enzymes, and receptors; as well as tissues, organelles, and other receptor probes.

The term "probe" or "capturing probe" as used herein generally refers to a molecular species and/or other markers that can bind to a specific analyte or target. Probes can comprise molecules and can be bound to the substrate, molecules, or other solid surface, directly or via a linker. Non-limiting examples of linkers include amino acids, polypeptides, nucleotides, oligonucleotides, and chemical linkers. A plurality of probes can be immobilized to a substrate, molecule or other solid surface and can be referred to as a probe array. A plurality of probes of a probe array may be arranged uniformly, for example as an arrangement of spots, or non-uniformly.

The term "about" or "nearly" as used herein generally refers to within +/−15%, 10%, 9%, 8%, 7%, 6%, 5%, 4%, 3%, 2%, or 1% of the designated amount.

The term "label" as used herein refers to a molecular structure that can be attached to a molecule (e.g., a target and/or a probe), to make the molecule detectable, distinguishable and/or traceable by providing a characteristic which may not be intrinsic to the target molecule. Examples of labels may include are luminescent molecules (e.g., fluorophores), reduction-oxidation (redox) species, or enzymes. In some cases, labels may comprise fluorophores with long lifetimes, such as, for example, lanthanide chelates and transition metal chelates, which are luminescent or phosphorescent.

The term "nucleotide," as used herein, generally refers a molecule that can serve as the monomer, or subunit, of a nucleic acid, such as deoxyribonucleic acid (DNA) or ribonucleic acid RNA). A nucleotide can be a deoxynucleotide triphosphate (dNTP) or an analog thereof, e.g., a molecule having a plurality of phosphates in a phosphate chain, such as 2, 3, 4, 5, 6, 7, 8, 9, or 10 phosphates. A nucleotide can generally include adenosine (A), cytosine (C), guanine (G), thymine (T) and uracil (U), or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. A nucleotide may be labeled or unlabeled. A labeled nucleotide may yield a detectable signal, such as an optical, electrostatic or electrochemical signal.

As used herein, the terms "polynucleotide", "oligonucleotide", "nucleotide", "nucleic acid" and "nucleic acid molecule" generally refer to a polymeric form of nucleotides (polynucleotides) of various lengths, either ribonucleotides (RNA) or deoxyribonucleotides (DNA). Examples of nucleotide sequences are sequences corresponding to natural or synthetic RNA or DNA including genomic DNA and messenger RNA. The length of the sequence can be any length that can be amplified into nucleic acid amplification products, or amplicons, for example, up to about 20, 50, 100, 200, 300, 400, 500, 600, 700, 800, 1,000, 1,200, 1,500, 2,000, 5,000, 10,000 or more than 10,000 nucleotides in length, or at least about 20, 50, 100, 200, 300, 400, 500, 600, 700, 800, 1,000, 1,200, 1,500, 2,000, 5,000, 10,000 or 10,000 nucleotides in length.

As used herein, the terms "peptide," "polypeptide," and "protein" are used interchangeably, and generally refer to a compound comprised of amino acid residues covalently linked by peptide bonds. Polypeptides may include any peptide or protein comprising two or more amino acids joined to each other by peptide bonds. Examples of polypeptides may include, for example, biologically active fragments, substantially homologous polypeptides, oligopeptides, homodimers, heterodimers, polypeptides and variants thereof, modified polypeptides, derivatives, analogs, fusion proteins, or combinations thereof. A polypeptide may be a natural peptide, a recombinant peptide, or a combination thereof.

As used herein, the singular forms "a", "an", and "the" include plural references unless the context clearly dictates otherwise.

The term "detector" as used herein generally refers to a device, generally including optical and/or electronic components that can detect signals.

TGF System Overview

The present disclosure provides methods, devices, reagents and systems based on time-gated fluorescence (TGF). The system may comprise a TGF based biochip. The TGF biochip may be semiconductor-integrated. In some cases, the semiconductor platform and manufacturing process through which the system is created is complementary metal-oxide-semiconductor (CMOS).

The methods and systems of the present disclosure may be used to detect, analyze, and/or quantify a plurality of analytes present in an aqueous sample through TGF transduction methods. The TGF CMOS biochip can be a monolithically-integrated biosensor array with addressable locations. See, e.g., U.S. Pat. Nos. 9,708,647, 9,499,861 and 10,174,367, each of which is entirely incorporated herein by reference. Each addressable location may comprise an independently operating TGF photo-sensor that detects TGF signals from its dedicated sensing area. The sensing/detection may be conducted in real-time and in the presence of an aqueous sample, or when such a sample is washed away. The TGF photo-sensor can adopt periodical charge integration (PCI) methods in which periodical signal accumulation is performed by applying multiple time-gated excitation pulses. The TGF CMOS biochip system can physically interface with the aqueous sample and apply physiochemical processes to the sample, including, for example, applying time-varying temperature profiles, biochemical reagents, or pulsed excitation photon fluxes to the sample.

Figure 2:
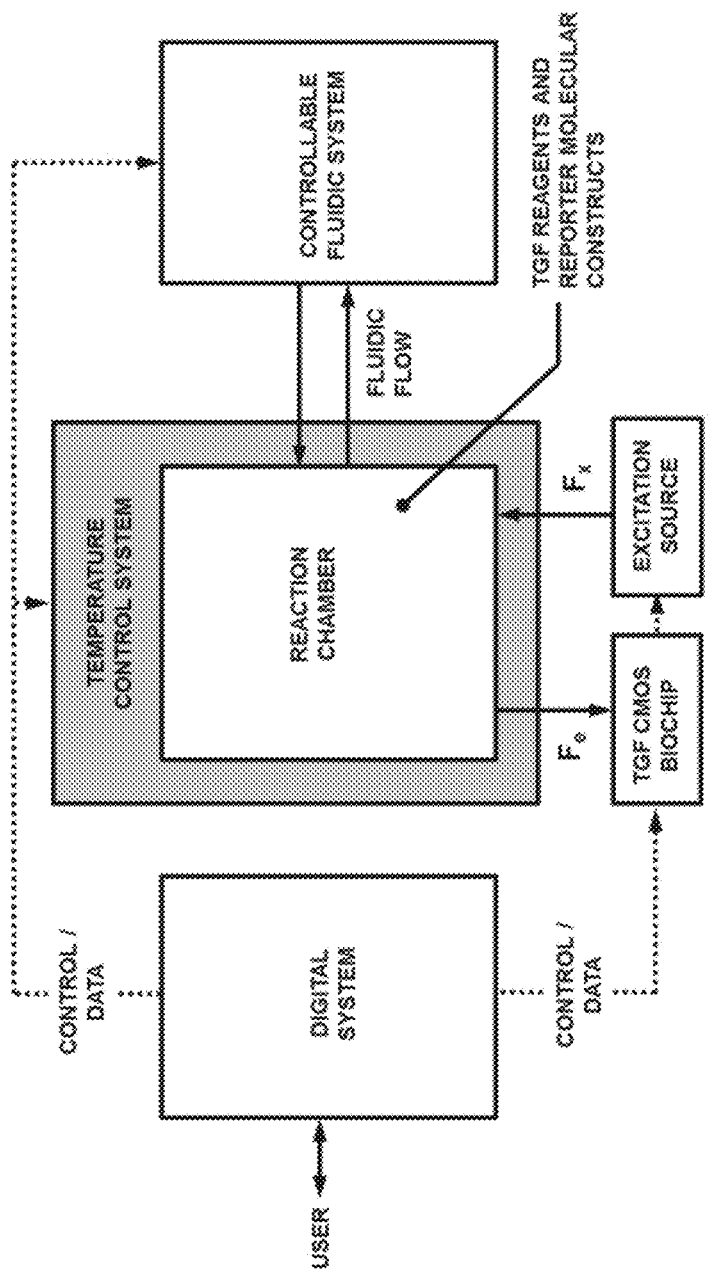
FIG. 2 illustrates architecture and functional blocks of an example time-gated fluorescence (TGF) system.

The TGF CMOS biochip system, as illustrated in FIG. 2, can comprise of components including, but not limited to:

1. TGF CMOS biochip which can identify and detect analytes interfaces to its top surface through TGF transductions methods in a 2D-array format;
2. Reaction Chamber which can interface the sample fluid (e.g., a fluidic aqueous sample that includes the analytes) with the TGF CMOS biochip;
3. Excitation Source which can introduce wavelength-specific photon flux into the reaction chamber and/or TGF CMOS biochip surface in a controlled fashion and synchronized with the TGF CMOS biochip operation;
4. Controllable Fluidic System configured to move into and/or, remove and/or, hold the reagents and/or sample from, and into, the reaction chamber in a controlled fashion and synchronized with the TGF CMOS biochip operation;
5. Temperature Controller which can set the temperature of the fluidic within the reaction chamber in a controlled fashion and synchronized with the TGF CMOS biochip operation; and
6. TGF Reagents and Reporter Molecular Constructs which can enable the detection of the analytes and targets by the TGF CMOS biochip within the reaction chamber and according to a specific assay methodology.
7. Digital System which can coordinate the operation of one or more components comprised in the system, collect the data and/or communicate the data to a processing and/or data analysis unit.

TGF CMOS Biochip

Figure 3:
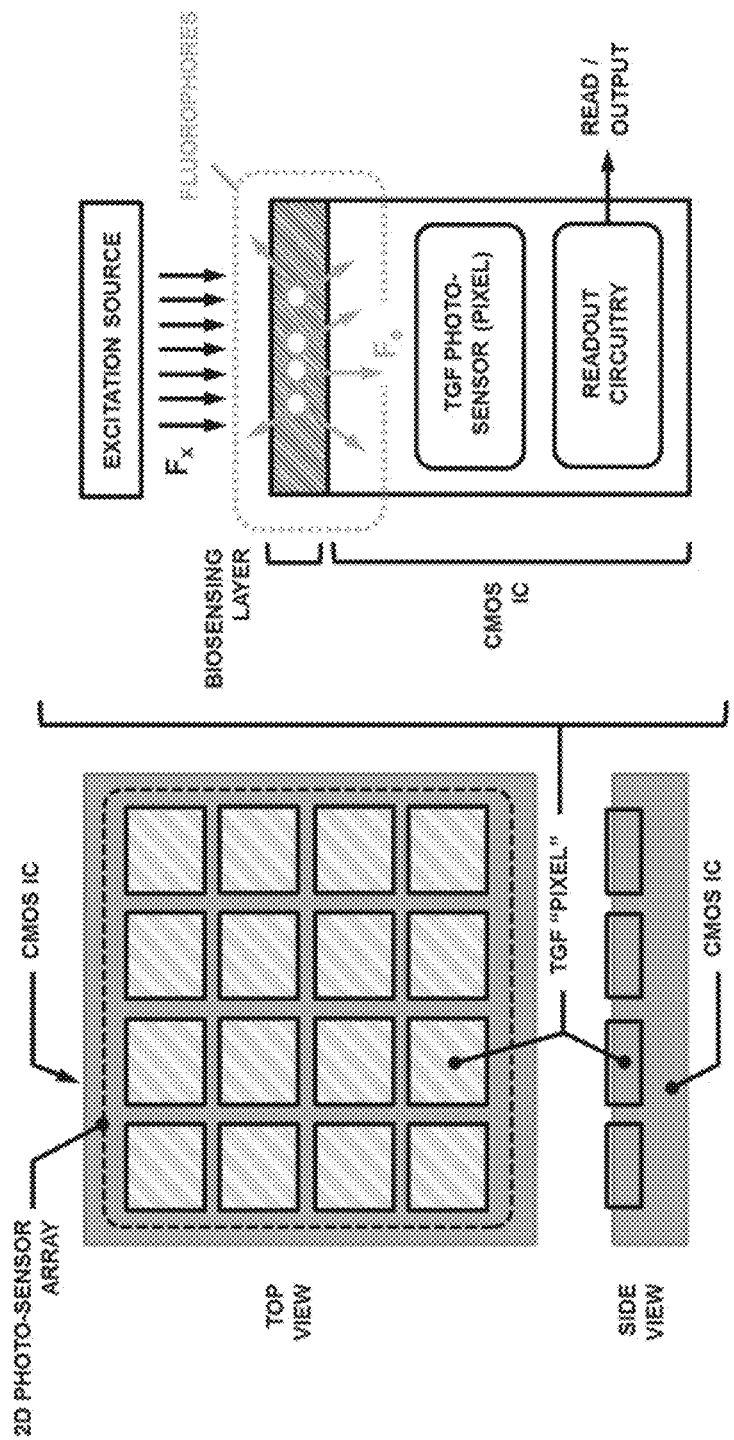
FIG. 3 illustrates architecture and functional blocks of an example time-gated fluorescence (TGF) complementary metal-oxide semiconductor (CMOS) biochip.

As shown in FIG. 3, The TGF CMOS biochip can comprise components including, but not limited to:

A. CMOS Integrated Circuit (IC), which can include the following functional blocks embedded within its monolithically-integrated semiconductor substrate:
  i. TGF photo-sensor array comprising a plurality of detectors in a 2D array format. The individual detectors (e.g., a "biosensing element" or "pixel") can measure the emitted photon flux from the fluorophores ($F_e$) at their addressable location, in parallel, simultaneously, and independently. The detectors can also adopt periodic charge integration (PCI) TGF methods;
  ii. Readout circuitry which may acquire data from individual TGF pixels and communicate them sequentially, in parallel, or a combination thereof, to an off-chip unit (external destination); and
  iii. On-chip passive resistive heater and temperature sensor.
B. Biosensing Layer, which can be located on a surface of the CMOS IC and can utilize TGF methods to create analyte-specific, localized TGF signal coupled with the TGF pixels. The biosensing layer may comprise a plurality of probes at independently (and/or individually) addressable locations on a solid surface. Each pixel can comprise a plurality of identical or different probes molecules that can specifically bind to or interact with a specific target/analyte or reagents in the reaction chamber;

CMOS Integrated Circuits (IC)

Figure 4:
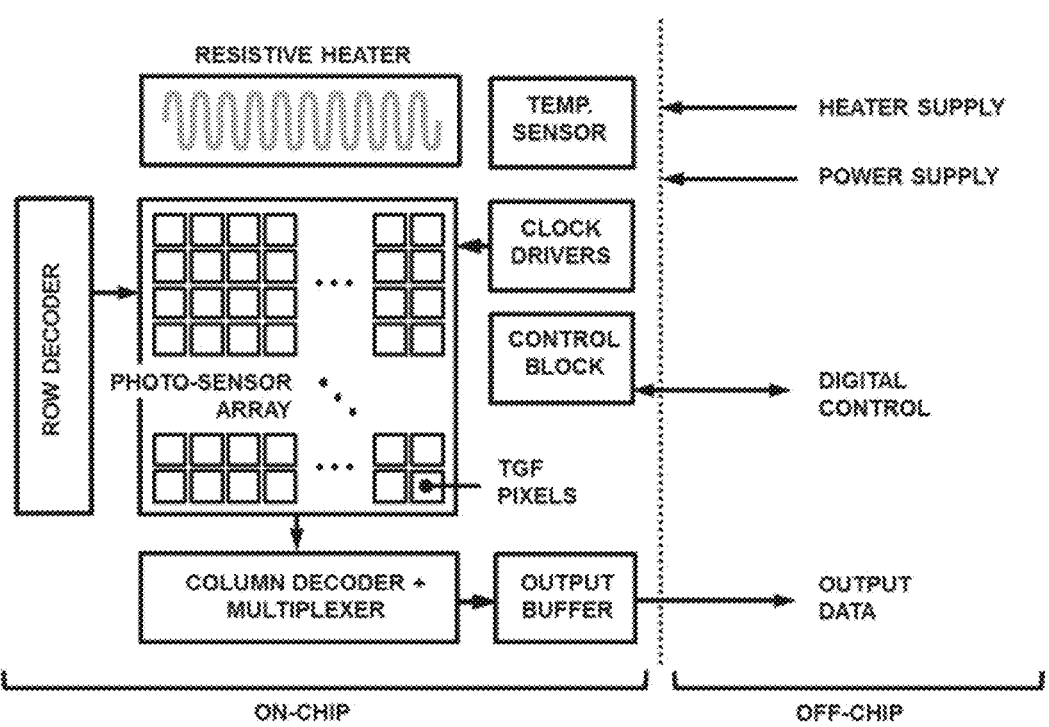
FIG. 4 illustrates architecture of an example CMOS integrated circuit (IC) for the TGF CMOS biochip system.

The architecture of the integrated CMOS IC for the TGF biochip is illustrated in FIG. 4. The CMOS die include a 2D photo-sensor array, with a similar general readout circuitry architecture to other biosensor arrays. See, e.g., U.S. Pat. Nos. 9,708,647, 9,499,861 and 10,174,367, each of which is entirely incorporated herein by reference. The photo-sensor array, where identical CMOS embedded TGF pixels are placed may be read sequentially (i.e., one pixel at a time) using a row and column decoder. The output of the chip, sent to off-chip through an output buffer, can be either analog or digital.

The chip may also include a resistive heater and a temperature sensor to accommodate the temperature control of the reaction chamber (e.g., Hassibi, A. et al. "A fully integrated CMOS fluorescence biochip for DNA and RNA testing," IEEE Journal of Solid-State Circuits, 52(11):2857-2870, 2017). In addition, the CMOS IC can also include a control block to be programmed and accessed off-chip by the user to set the functionality of the chip and manage the data acquisition.

Figure 5:
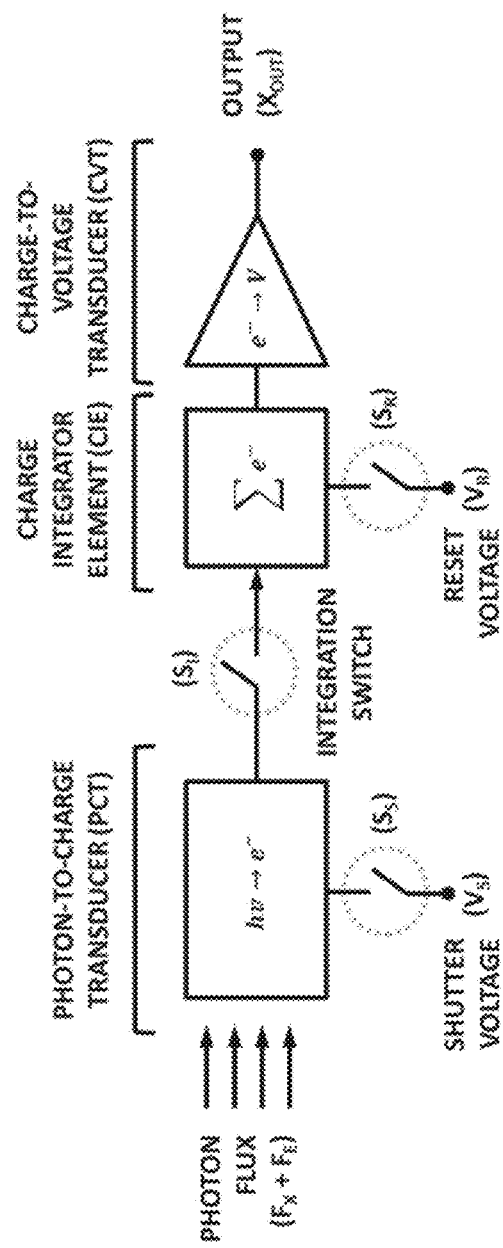
FIG. 5 shows topology of an example TGF pixel with an electronic shutter and periodic charge integrating (PCI) capability.

The general topology of an example TGF pixel is shown in FIG. 5. The TGF receive both $F_e$ and $F_x$ from the addressable location on its biosensing layer and the photons may be converted into electrical charge by using a photon-charge transducer (PCT). Examples of PCT in CMOS processes include lateral photodiodes (e.g., Cauwenberghs, G., et al. "Which photodiode to use: A comparison of CMOS-compatible structures," IEEE sensors journal, 9(7):752-760, 2009), or pinned photodiode devices (e.g., Hondongwa, D. B. et al. "A review of the pinned photodiode for CCD and CMOS image sensors," IEEE J. Electron Devices Soc., 2(3):33-43, 2014). The PCT device may comprise two switches connected to it. The first may be an electronic shutter switch ($S_S$) which removes the charge completely out of the PCT through connecting it to the electronic shutter voltage source ($V_S$). The second may be an integration switch ($S_I$) which transfer the created charge into a charge integrator element (CIE). The CIE device may be continually connected to a charge-to-voltage transducer (CVT) to produce a TGF pixel output. In addition, the CIE may have a reset switch ($S_R$) to remove the integrated charge at any time and basically "reset" the CIE output value to $V_R$.

Figure 6:
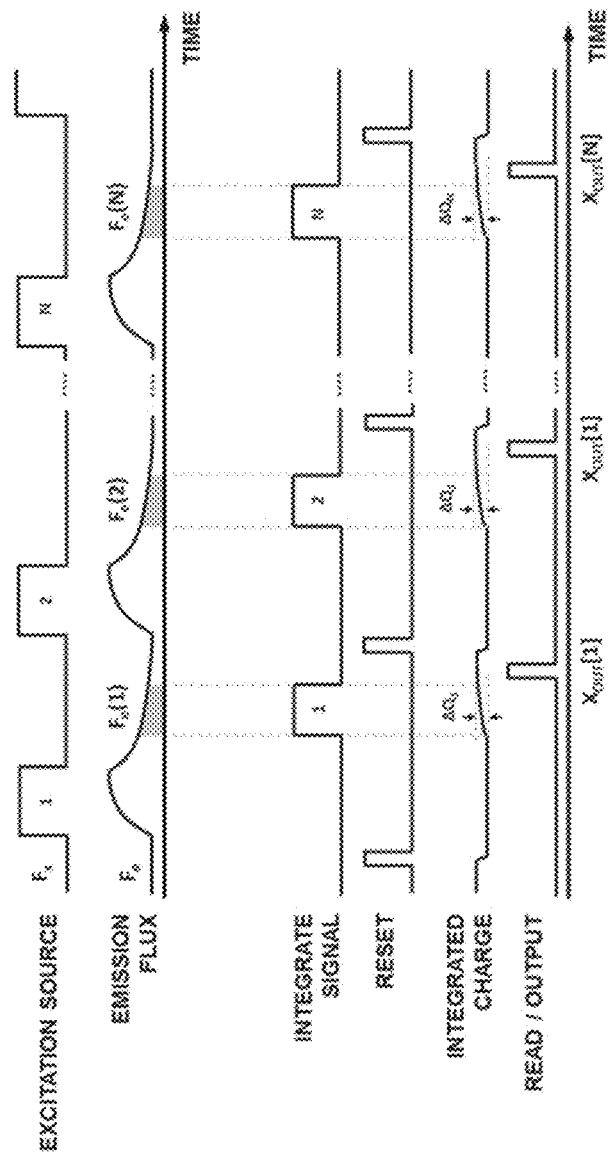
FIG. 6 shows timing diagram of a conventional TGF system.

TGF pixel of the present disclosure may be different from conventional detectors for TGF or time-resolved fluorescence. One difference is the absence of the $S_S$ and $S_I$ and the capability of selectively discarding or integrating the generated charge of the PCT. In FIG. 6, an example timing diagram for the operation for a conventional TGF system is shown. As FIG. 6 shows, $F_e$ is measured after every N individual $F_x$ pulse by quantifying the photo-induced charge during integration time intervals. The N outputs ($X_{OUT}[1]$ to $X_{OUT}[N]$) are then averaged to estimate, $F_e$. Multiple challenges and non-idealities may exist with this system. For example:

It may be needed to take N consecutive measurements (reads) to estimate $F_e$ or every pixel. Since $F_e$ may be low, extensive averaging may be required and, for example, values of N>100 may be needed in such TGF systems.

Due to the low level of signal (e.g., 10 total electrons per $F_e$ pulse), CVT may require very high gain (e.g., >20 µV/e) with an analog-to-digital quantization noise of equivalent to less than a few electrons per read.

When large biosensor arrays may be implemented with number of pixels M>1000, the number of reads per frame becomes N×M which can become quickly overwhelming. For example, if a fluorophore used in TGF has a lifetime of $\tau_L$=100 ns, it is possible to create the $F_x$ pulse sequence with period 1 ms=10 $\tau_L$. If N=100 and M=1000, then the readout speed will be $10^5$ reads/ms or 100 million sample/s. Given the noise requirements of the system, this may require very complex readout circuitry and call for a significant amount of power. As a result, one may consider reducing the pulse sequence frequency and essentially slowing down TGF measurements.

Figure 7:
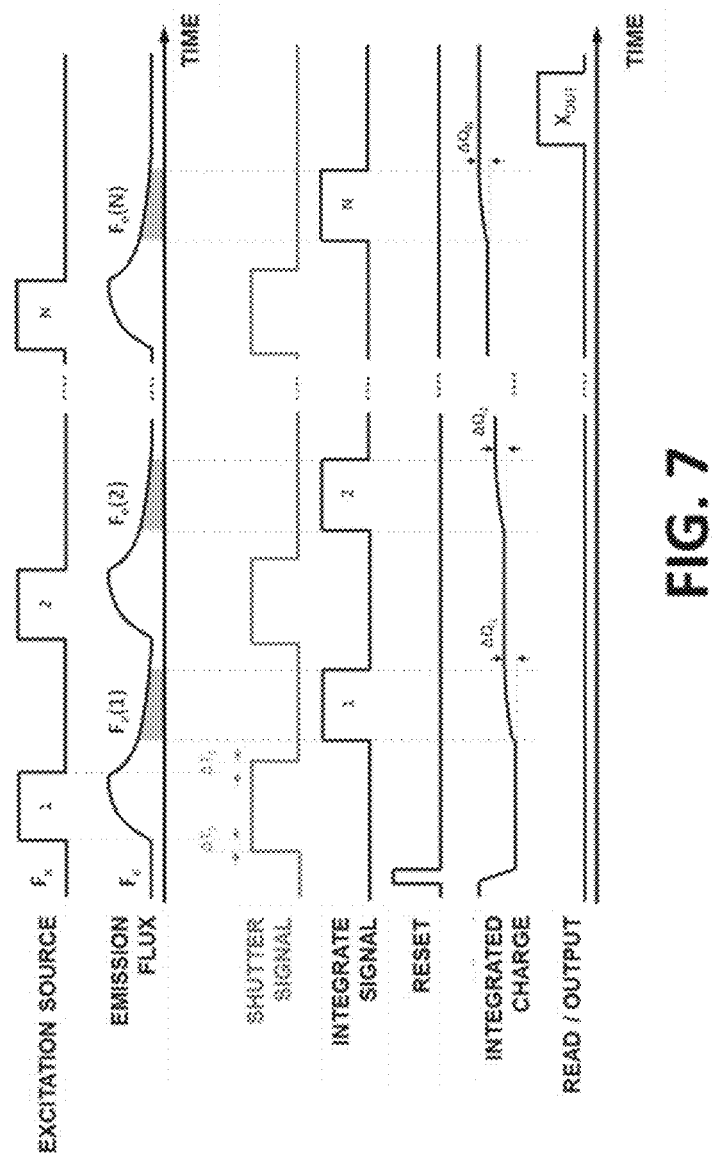
FIG. 7 shows timing diagram of an example periodic charge integrating (PCI) TGF pixel.

In the present disclosure, by using the topology shown in FIG. 4, the above-mentioned challenges may be addressed. FIG. 7, depicts a timing diagram of the TGF pixel of the present disclosure, which adopts an in-pixel periodic charge integration (PCI) scheme to improve both the speed and performance of the TGF measurements. As FIG. 7 shows, by using $S_S$ and $S_f$ and applying an electronic shutter, responses of N pulses of the PCT may be integrated into the CIE which may create a single output. This may enable a readout of output once every N pulses with an amplitude N times larger than conventional TGF. Additional advantages to this approach may include, but are not limited to:

One read in PCI-TGF may be equal to N reads in conventional TGF.

The accumulated charge and the output amplitude signal of PCI-TGF may be N times of conventional TGF and can be read N times slower. Therefore, PCI-TGF can use a much more relaxed the readout circuitry with lower speed and signal higher chain quantization noise.

When large biosensor arrays, with number of pixels, M>1000 elements are used, the required readout and pixel scanning speed requirement may be N times less than conventional TGF. Therefore, it may become quite feasible to create arrays with M>$10^6$, a number that may be necessary for the adoption of for massively parallel arrays used in life-science research.

The challenges in the implementation of PCI-TGF may revolve around the circuit and device implementation of the switches, efficient approaches of transferring charge in time intervals compatible with TGF, and CIE.

Biosensing Layer

The biosensing layer as provided herein may include an organic layer that may be created on top of a CMOS IC and interfacing the reaction chamber to: (a) form addressable location(s) for probes on top of the pixels; and (b) enable TGF transduction by first capturing targets and subsequently creating TGF signals as a function of the probe target interactions and/or structure of the captured target.

Biosensing layers may be created by various methods. For example, specific probe structures may be physically printed, immobilized, or spotted or chemically synthesized on a surface. In some cases, probes are first randomly distributed within the array 2D surface and then identified prior to detecting the targets by alternative approaches that are known in the field. In some cases, the surface of the IC (typically made of $SiO_2$ or $Si_3N_4$) may be chemically modified with linkers and/or thin film structures to become compatible with probe attachment.

Figure 8:
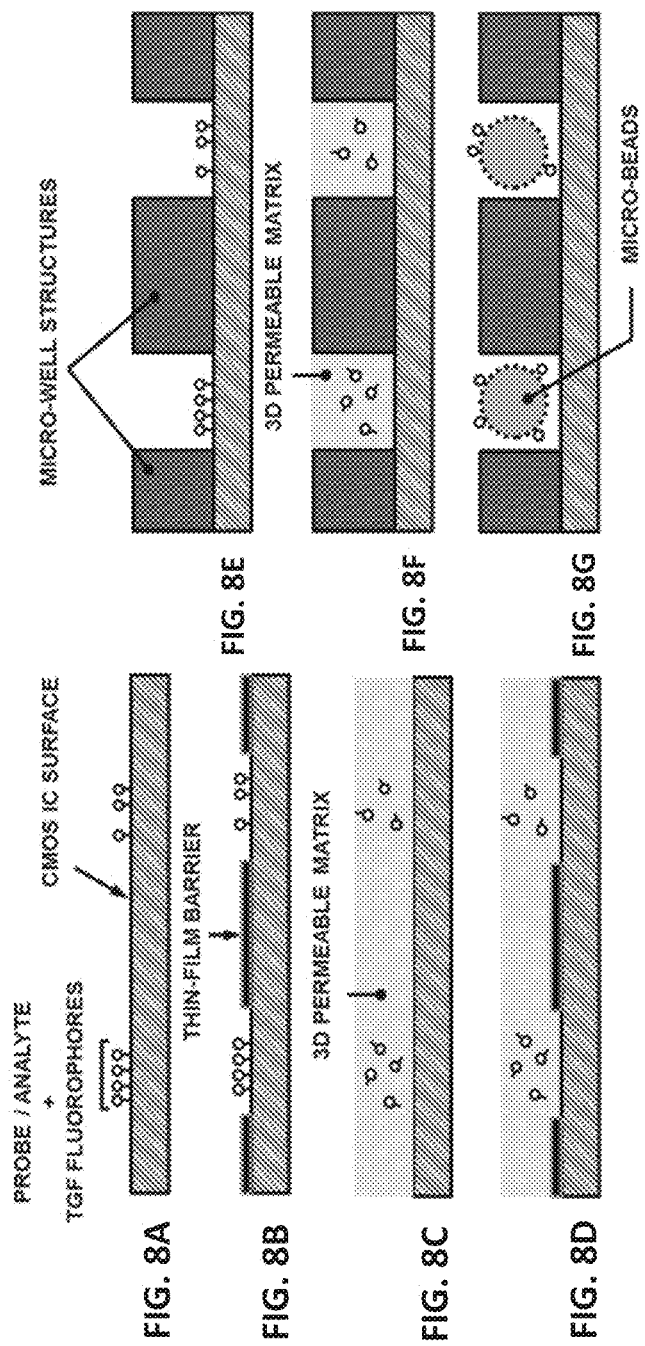
FIG. 8A shows a planar surface configuration of a biosensing layer structure for a TGF CMOS biochip in accordance with one of the embodiments of the present disclosure.
FIG. 8B shows a planar surface configuration of a biosensing layer structure for a TGF CMOS biochip with a thin film barrier in accordance with one of the embodiments of the present disclosure.
FIG. 8C shows a configuration of a 3D and permeable matrix coated on the surface of a biosensing layer for a TGF CMOS biochip in accordance with one of the embodiments of the present disclosure.
FIG. 8D shows a configuration of a 3D and permeable matrix coated on the surface of a biosensing layer with a thin film barrier for a TGF CMOS biochip in accordance with one of the embodiments of the present disclosure.
FIG. 8E shows a microwell configuration for a biosensing layer of a TGF CMOS biochip in accordance with one of the embodiments of the present disclosure.
FIG. 8F shows a microwell configuration for a biosensing layer with a 3D and permeable matrix coating the microwell for a TGF CMOS biochip in accordance with one of the embodiments of the present disclosure.
FIG. 8G shows a configuration of a combination of microwells and micro-beads with immobilized beads for a TGF CMOS biochip in accordance with one of the embodiments of the present disclosure.

FIG. 8 shows examples of biosensing structures that are compatible with CMOS ICs and TGF transduction methods, including PCI-TGF. In FIG. 8A and FIG. 8B, a planar surface may be implemented to immobilize probes and an addressable array may be created with and without a thin film barrier, respectively. In FIG. 8C and FIG. 8D, a 3D and permeable matrix may be coated on the surface to allow for probe immobilization at the intimate proximity of the surface) In FIG. 8E and FIG. 8F, microwells may be used to better isolate the immobilized probes and isolate the TGF pixels. In FIG. 8G, a combination of microwells and microbeads with immobilized beads may be used to create an addressable array.

Reaction Chamber

The reaction chamber as provided herein may be a fluidic chamber that interfaces with the CMOS TGF biochip and contains the fluidic sample with analytes, targets, and other biochemical reagents that are required for the execution of the TGF assay.

The volume of this reaction chamber can be between about 0.1 μL to 10,000 μL, e.g., between about 1 μL to 100 μL.

The reaction chamber may comprise a plurality of inlets and outlets to accommodate the interfacing with the controllable fluidic system to insert or remove fluids.

To accommodate TGF, the fluidic system can provide a transparent optical travel path for the pulse F to go through the fluidic and reach the biosensing layer. The transmittance in the wavelengths of $F_x$ can be from 1% to 99.9%, but typically is from 5% to 80%.

The reaction chamber can be built using a variety of materials such as polymers, glass, semiconductor, crystals, or ceramics materials, or a combination of them.

Excitation Source

The excitation source as provided herein may comprise an optical light source that can create a wavelength selective photon flux ($F_x$) with a controllable and time-varying amplitude. The light source may illuminate the biosensing layer of the system and the coordinates in which TGF transduction takes place.

The excitation source center wavelength can be anywhere between about 200 nm to 1500 nm, e.g., between about 300 nm to 800 nm.

The excitation source spectral span (bandwidth) may be from about 1 nm to 500 nm, e.g., from about 10 nm to 100 nm.

The excitation source photon flux may be directional and may be optically collimated.

The excitation source peak output power may be from about 10 mW to 100 W, e.g., from about 100 mW to 10 W.

The excitation source power may be controllable and modulated with bandwidth of up to about 1 GHz, e.g., up to about 1 MHz The excitation source turns off and on times may be as fast as about 0.1 nanosecond (ns), e.g., as fast as about 1 microsecond (μs).

Controllable Fluidic System

The controllable fluidic system introduces into, and/or removes from, and/or confines within the reaction chamber aqueous media that can include samples and assay reagents, and/or TGF transduction reagents in a controlled fashion by the user. The workflow and sequence of each fluidic operation may be defined by the assaying method and can be, for example, flow-through and mono-directional, or closed-tube.

The controllable fluidic system may use fluidic components such as pumps, valves, and tubing to perform the workflow.

Temperature Controller

The temperature controller system can establish a specific temperature for the fluidic of the reaction chamber, and/or create a temperature profile that requires heating and/or cooling. A temperature controller can include a feedback control system that measures the temperature, using temperature sensors within the CMOS biochip IC and/or sensor devices coupled with the reaction chamber (such as a thermistor or a thermocouple), and, based on the measured temperature, add or remove heat from the reaction chamber using CMOS biochip IC heaters and/or thermal devices (such as Peltier devices or resistive heaters). Temperature controllers can comprise heat sinks for removing heat. Temperature controllers can have components within the CMOS IC, including resistive heaters and/or temperature sensors.

Temperature controllers can change the temperature of a substrate, reaction chamber, or array pixel. The rate of temperature change can be about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20° C./minute. The rate of temperature change can be at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20° C./minute. The rate of temperature change can be at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20° C./minute. Temperature controllers can change temperature at a linear rate (e.g., 5° C./second). Alternatively, temperature controllers can change temperature at a non-linear rate. Temperature controllers can increase or decrease temperature.

Digital System

The digital system is essentially a computing and controlling digital hardware And embedded software than can control and coordinate the functionality of the components of the system.

TGF Reagents and Reporter Molecular Constructs

To enable TGF transduction, we can use molecular structures and constructs that exhibit fluorescence activity. Such molecular structures are sometimes referred to as fluorophores (or fluorochromes, similarly to chromophores) which are chemical compound that can re-emit light upon light excitation with life-times from about 10 ps to 10 ms, e.g., from about 1 ns to 100 ns.

As provided herein, various types of fluorophores can be adopted by a TGF system. In some cases, fluorophores that have longer life-times, e.g., greater than about 100 ns, may be used. In cases where fluorophores with longer lifetime are used:

Longer life-time fluorophores may require lower speed PCI-TGF systems in the CMOS Biochip IC;

The excitation source switching speed can be more manageable, and more cost-efficient light sources can be used; and The negative effects of background autofluorescence from the biological sample and/or materials in the fluidic chamber and/or biolayer may be mitigated, if the they have shorter life-time compared to the adopted TGF fluorophore.

TGF systems may not need an excitation and emission filter set, or other filters of wavelength to transmit a desired signal for an analyte and/or remove background fluorescence from signals of the analyte. In some cases, the emission filter may filter out violet, blue, green, yellow, orange, and red light, or any combination thereof.

Various types of fluorophores may permit multi-color capabilities. In TGF, differentiating fluorophores may be determined by the differences in their fluorescence lifetimes after excitation. In some cases, these fluorophores can be reactive and/or conjugated dyes, nucleic acid dyes, fluorescent proteins, and cell function dyes. Once emission light is pulsed in the direction of a substrate containing the fluorophore species, a shutter may close off the detection apparatus from the emission light and the reflected emission light. The shutter may be removed to let in the desired fluorescent light. A first fluorophore with a shorter lifetime can be detected among the detected signals if the shutter opens shortly after the emission is stopped. A second fluorophore with a longer lifetime can be detected if the shutter is opened after waiting for a longer time after the emission is stopped. In this scenario, the second fluorophore (longer lifetime) may be detected with little or no interference of the first fluorophore (shorter lifetime). In addition, readings of the signals corresponding to the first fluorophore (shorter lifetime) in the presence of the second fluorophore (longer lifetime) can be estimated or calculated by calibration of the detected signals using information about the second fluorophore (longer lifetime) detected and/or determined later. Other experimental designs for the multiplex detection of multiple fluorophores are possible with or without the use of emission and excitation filter sets. Accordingly, multiple fluorophores can be detected in a single experiment by the opening and closing of the shutter following the emission in the absence of excitation and emission filter sets. Individual species of fluorophores can be detected based on the differences in their decay rates by varying the delay profiles of the shutter and the time during which the shutter is opened. The multi-color capability may be limited by shutter speed and the overlap between fluorescence decay rates of the fluorophores to be detected.

For example, in some examples, metal chelate, such as Lanthanide chelates can be used as TGF fluorophores. In some cases, TGF fluorophores may predominantly act as molecular reporters in TGF assays either as a standalone reporter or an element (donor or acceptor) in a fluorescence energy transfer moiety. Examples include, but are not limited to, Forster Resonance Energy Transfer (FRET) technologies. See Song, Y., et al., "Development of FRET assay into quantitative and high-throughput screening technology platforms for protein-protein interactions," *Annals of biomedical engineering* 39(4): 1224-1234, 2011. The role of TGF fluorophores may include facilitating the generation of a specific TGF signal that may be correlated to the presence or absence of a molecular reaction or presence or absence of a specific target molecule.

TGF fluorophores can be used as labels for specific target analytes, in applications where the targets can be chemically modified to incorporate a TGF fluorophore. Examples includes, but are not limited to, Northern blots, Southern blots, DNA microarrays, quantitative Polymerase Chain Reaction (PCR), digital PCR, and diagnostic assays.

In microarrays and Northern blots, the mRNA target analyte may be converted into a fluorophore-labelled complementary DNA (cDNA), for example, through reverse transcription.

In Southern blots, a fluorophore-labeled cDNA may be used to identify a target sequence.

In quantitative polymerase chain reaction (PCR) and digital PCR (dPCR), the fluorophore may be incorporated into an amplified nucleic acid sequence or a primer sequence to demonstrate the accumulation of a target sequence (See, e.g., Y. Wong et al., "Applications of digital PCR in precision medicine," Expert Review of Precision Medicine and Drug Development 2(3): 177-186, 2017).

In a diagnostic assay, a device may be used to sequester target nucleic acids, and a fluorophore-labelled cDNA may be used for direct detection.

TGF fluorophores can also be used as labels for the detection of probes in sandwich assays. Examples include, but are not limited to, Western Blots, Enzyme-Linked Immunosorbent Assay (ELISA), Enzyme-Linked Immuno SPOT (ELISPOT) including FluoroSpot (See, e.g., G. Kesa et al., "Comparison of ELISpot and FluoroSpot in the Analysis of Swine Flu-Specific IgG and IgA Secretion by in Vivo Activated Human B Cells," Cells 1(2): 27-34, 2012), and protein arrays.

- In these methods, the TGF fluorophores may be used as a direct method for detection, in which the fluorophore is conjugated to the primary detection antibody.
- In these methods, the TGF fluorophore may also be used as an indirect method for detection, in which the fluorophore is conjugated to a secondary antibody.
- ELISPOT is a type of assay that quantitatively measures the frequency of cytokine secretion for a single cell. The ELISPOT Assay is also a form of immunostaining that uses antibodies to detect an analyte, including but not limited to, any biological or chemical substance being identified or measured, such as, for example, protein analyte.
- The FluoroSpot Assay is a variation of the ELISpot assay. The FluoroSpot Assay uses fluorescence to analyze multiple analytes. It can detect the secretion of more than one type of protein or other analytes.

TGF fluorophores can be used as labels in cell sorting, counting, and detecting methods. An example may be flow cytometry, in which cells are labeled with a fluorophore.

- In this method, the cells may be sorted and counted by their fluorescence profiles.
- In this method, the specific cellular characteristics and/or functions may be identified by their fluorescence profiles.

TGF fluorophores can be used in applications where solid-phase and immobilized probes are labeled. Examples are inverse fluorophore assays (e.g., A. Hassibi et al., "Multiplexed identification, quantification and genotyping of infectious agents using a semiconductor biochip," Nature biotechnology, 36(8):738-745, 2018)

TGF fluorophores can be used in assays in which the chemical reactions are monitored while a target molecule is introduced to a reacting reagent. The target molecule and/or the reacting reagent may include TGF fluorophores. Examples are Sanger sequencing, Next Generation Sequencing (NGS) assays such as sequence-by-synthesis (SBS) (See, Ansorge; Metzker; and Pareek et al., "Sequencing technologies and genome sequencing," J. Appl. Genet., 52(4):413-435, 2011), sequence-by-hybridization (SBH) (See, Qin, Schneider and Brenner, "Sequencing by Hybridization of Long Targets," PLoS One., 7(5):e35819, 2012), and pyrosequencing.

- In this method, Single Molecule Real Time (SMRT) sequencing and Illumina sequencing can use TGF fluorophore-labeled nucleotides to determine the sequence of a nucleic acid Sequence information of nucleic acids may be used to improve people's lives. (See, e.g., Ansorge, W., "Next-generation DNA sequencing techniques," New Biotech. 25(4):195-203, 2009). Several DNA sequencing platforms have been commercially available. The availability of parallel NGS technologies may enable the comprehensive analysis for biological targets, including but not limited to genomes, transcriptomes and interactomes. (See, e.g., Shendure, J. and Ji, H., "Next-generation DNA sequencing," Nature Biotech. 26:1135-45, 2008). However, although NGS technologies may produce comprehensive results, their turnaround time may be too slow to address the rapid progression of an infectious process in critically ill patients. In addition, while multiplexing a large number of target amplification reactions (e.g., multiplexed PCR) may be possible, but it is not straightforward to detect multiple amplicons simultaneously.

Commercially available NGS sequencing platforms may include the Illumina Genome Analyzer, the Roche (454) Genome Sequencer, the Life Technologies SOLiD platform, and real-time sequencers such as those from Pacific Biosciences. These platforms may require the construction of a set of DNA fragments from a biological sample. In most cases, the DNA fragments are flanked by platform-specific adapters.

Example 1

Figure 9:
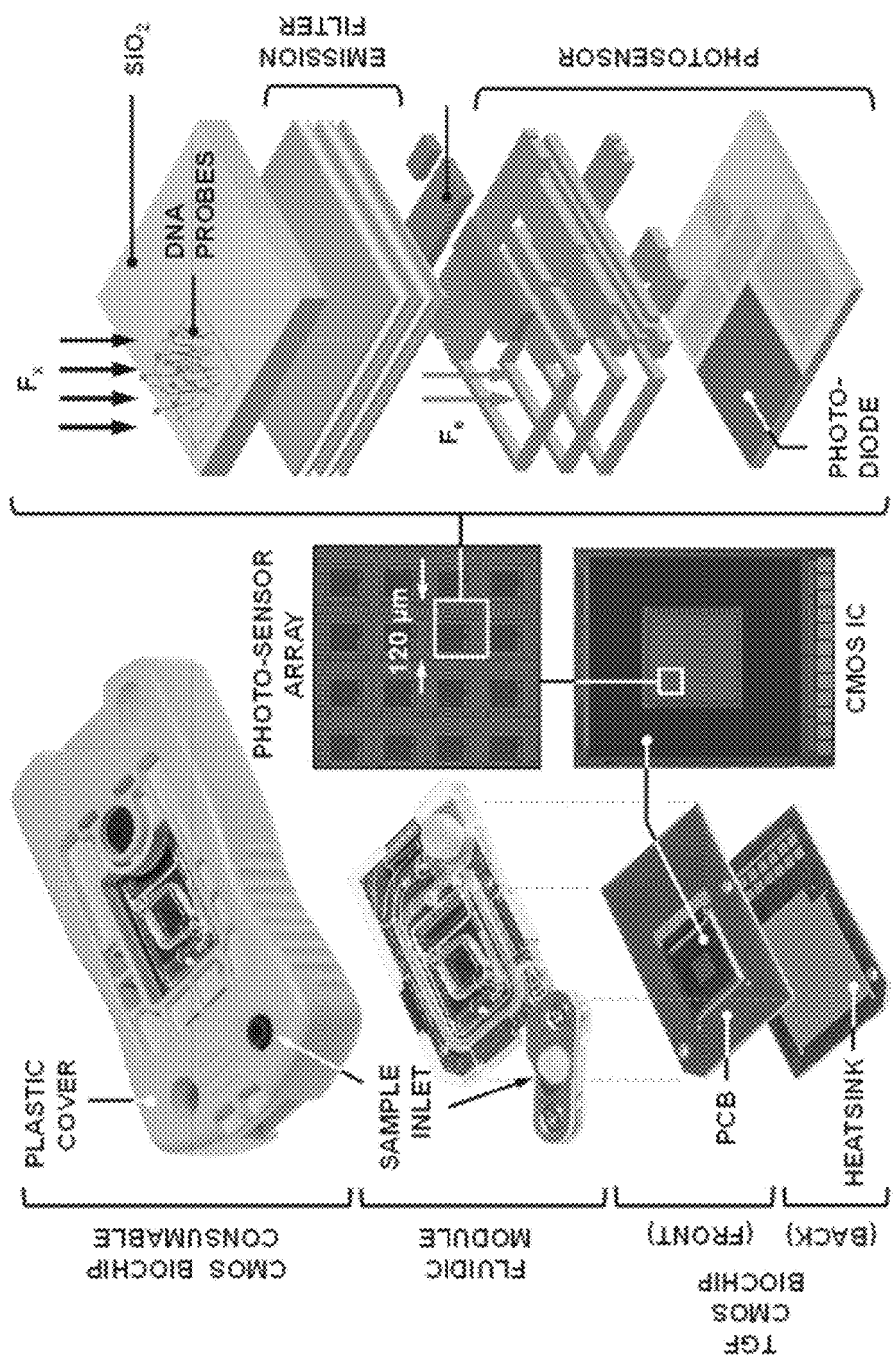
FIG. 9 shows an example TGF CMOS biochip module and its TGF pixel structure in accordance with one of the embodiments of the present disclosure.

In this example, a fully-integrated TGF CMOS biochip is presented that is specifically designed for DNA and protein addressable arrays of biotechnology. As shown in FIG. 9, a CMOS IC is assembled on a printed circuit board (PCB) substrate and then integrated with the fluidic module to create the biochip consumable. The biochip IC includes an array of 1024 biosensors pixels with an optical density (OD)~5.8 integrated emission filter and addressable (unique) immobilized probes (DNA) on every pixel. Pixel-level photo-sensors with Nwell-Psub photodiodes (acting as the PCT elements) are designed to be shot-noise-limited and offer >130 dB detection dynamic range (DDR). A temperature control and cycling system is also integrated in this biochip to accommodate thermal control. For that reason, a bandgap temperature sensor and a resistive heater are integrated that together can achieve heating/cooling rates of +/−10° C./s with an overall accuracy of ±0.25° C. within 25° C. to 100° C. range.

Figures 10A, 10B:
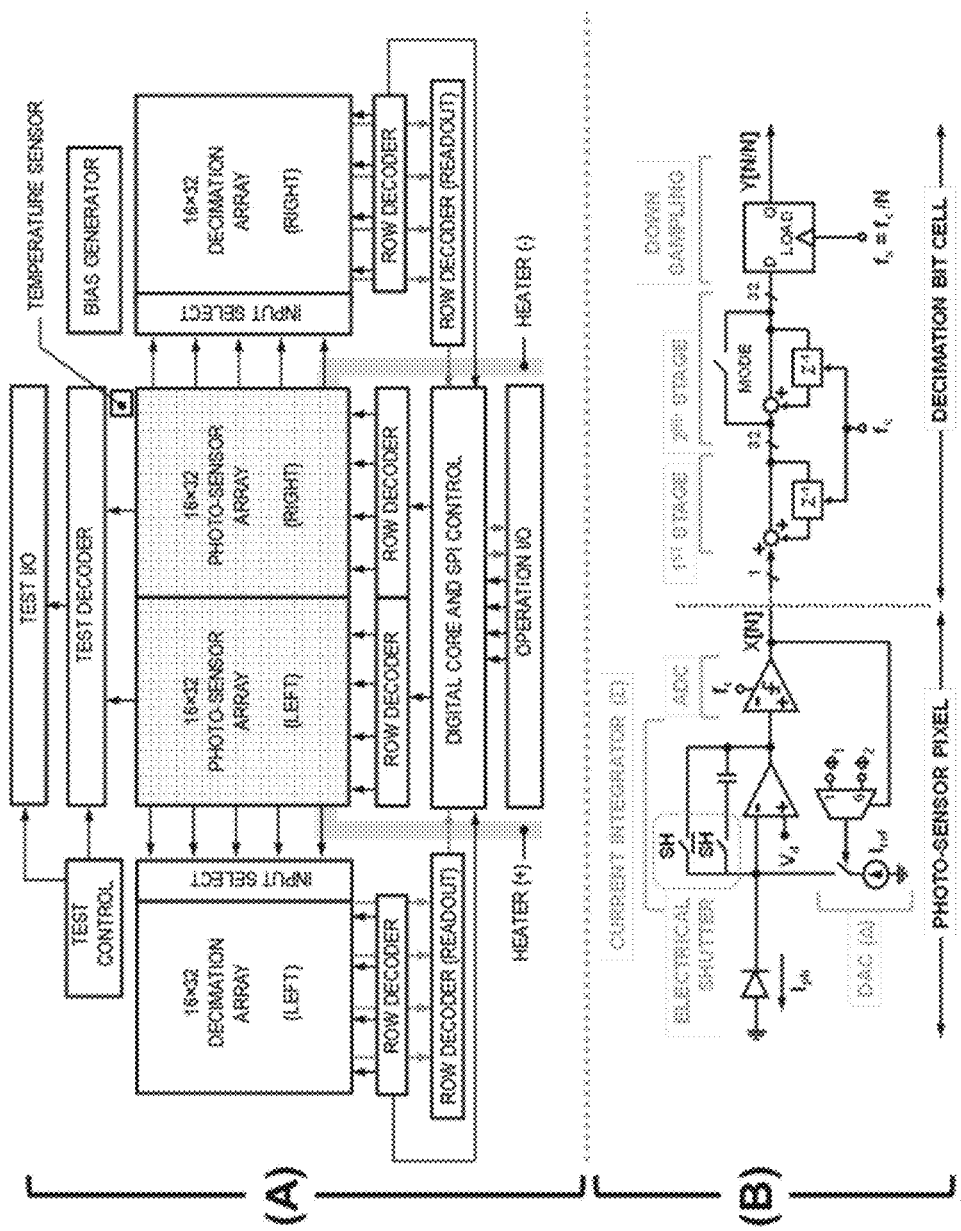
FIG. 10A shows architecture of an example biochip in accordance with one of the embodiments of the present disclosure.
FIG. 10B shows an example TGF pixel and its dedicated decimation cells in accordance with one of the embodiments of the present disclosure.

The architecture of the chip and 120 µm-pitch biosensing pixels and decimation cells are shown in FIG. 10A and FIG. 10B. The TGF pixels within the 32×32 array include a $\Delta\Sigma$ current detector that takes the photocurrent, $I_{ph}$, as its input and produces a 1-bit digital output stream that is transferred into the on-chip decimation array. The photo-sensor circuitry (FIG. 10B) includes a current integrator (acting as the CIE+CVT), a clocked comparator (ADC) and a programmable current source (DAC).

In the CWF mode (i.e., no pulsed excitation source or electronic shuttering), the $\Delta\Sigma$ current detector operates continuously with frequency of $f_c$ while the decimation cell implements a $sinc^2$ filter, by performing a two-stage 32-bit accumulation followed by down-sampling and readout with frequency of $f_s$. In the TGF mode, similar operation is done, but with the exception of periodic activation of an electronic shutter capable of diverting $I_{ph}$ from the integrator. This operation blocks the optical excitation pulses and reduces the natural autofluorescence background from biological media that typically have lifetimes <50 ns. The chip then accumulates and measures the fluorescence emissions at pre-programmed time intervals.

In this chip, the TGF pixels, the decimation arrays, bandgap temperature sensor, and reference voltage DACs are all operated and read by a single digital core block operating at 50 MHz and is accessible through a serial peripheral interface (SPI) port (FIG. 10A). The single resistive heater can provide up to 20 W using an external source, has a serpentine structure, and is uniformly distributed in the top metal layer. This chip can be fully operated using 14 pins (and bond wires) aggregated on one side of the die to facilitate efficient fluidic assembly and consumable manufacturing (FIG. 9).

Figure 11:
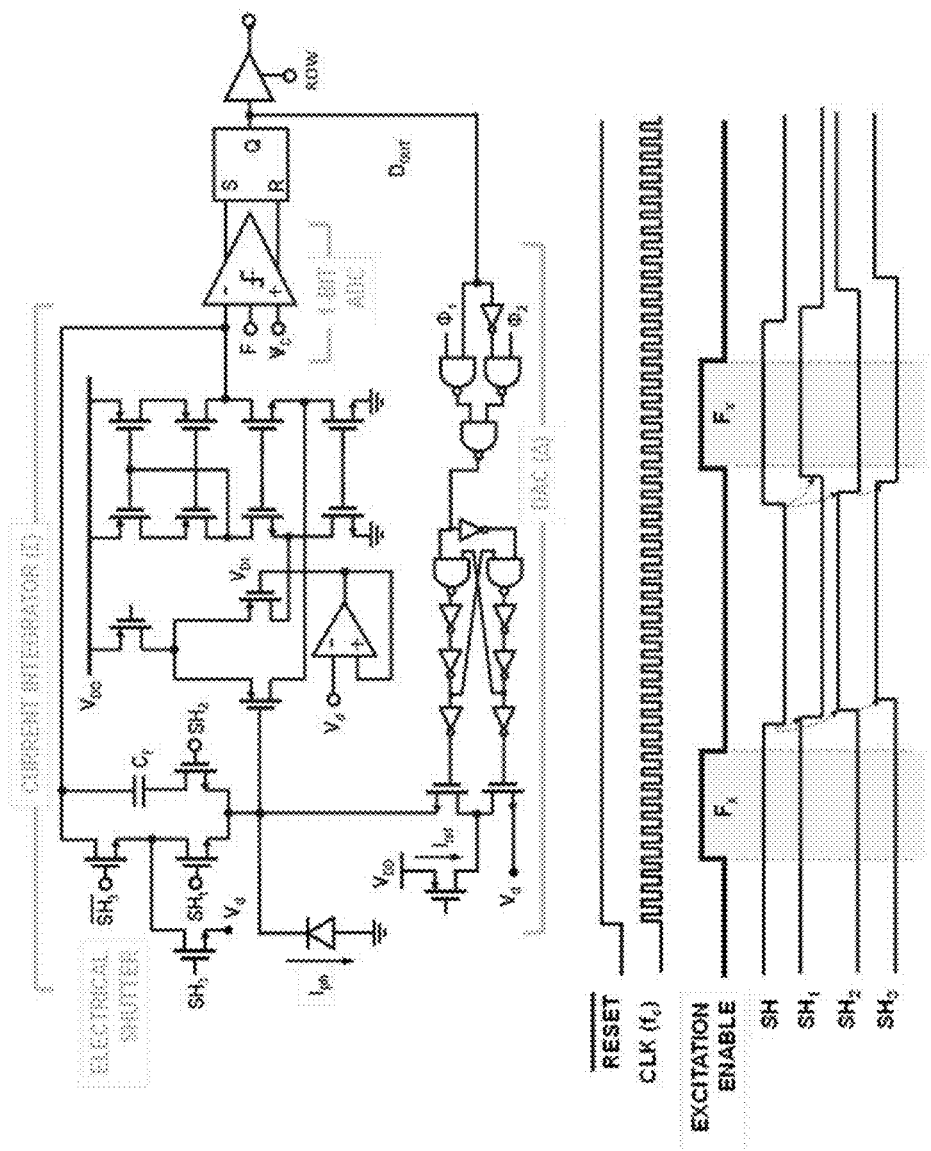
FIG. 11 shows photo-sensor pixel schematic and timing diagram of an example TGF mode in accordance with one of the embodiments of the present disclosure.

In FIG. 11, the schematic and timing diagram of the photo sensing pixel in the TGF mode is depicted. A capacitive trans-impedance amplifier (CTIA) is used as the CIE+CVT and a clocked comparator creates the pixel output, $D_{out}$. The DAC is implemented by using a current source that can be used to apply a current pulse into the CTIA input with two adjustable durations ($\Phi_1$ and $\Phi_2$). The electronic shutter uses $SH_1$, $SH_2$, and $SH_3$ to temporarily remove $C_f$, the feedback capacitor of the CTIA, out of the circuit and simultaneously shorting $I_{ph}$ to $V_d$ using the op-amp. Due to transistor mismatch, a small quantity of charge is injected into $C_f$ at every shutter operation that manifests itself as a pixel-dependent electronic shuttering offset current, $I_s$. This current when added to dark current $I_{dc}$, forms the random offset current of the pixel $I_o=I_s+I_{dc}$, which, in both CWF and TGF modes, is measured and extracted to estimate $I_{ph}$. This is done using a CDS approach in which one frame with excitation light and one without are taken, and then the measurements are subtracted from one another.

The decimation array has a dedicated bit cell for every pixel. The bit cell consists of a 32-bit incrementor, followed by a 32-bit adder, forming the two-stage accumulation unit (FIG. 10B). At intervals of $T=1/f_s$, the output of the adder is loaded onto the 32-bit shift register. The data from the shift registers are then passed into the digital unit in a serial scan chain fashion.

Figure 12:
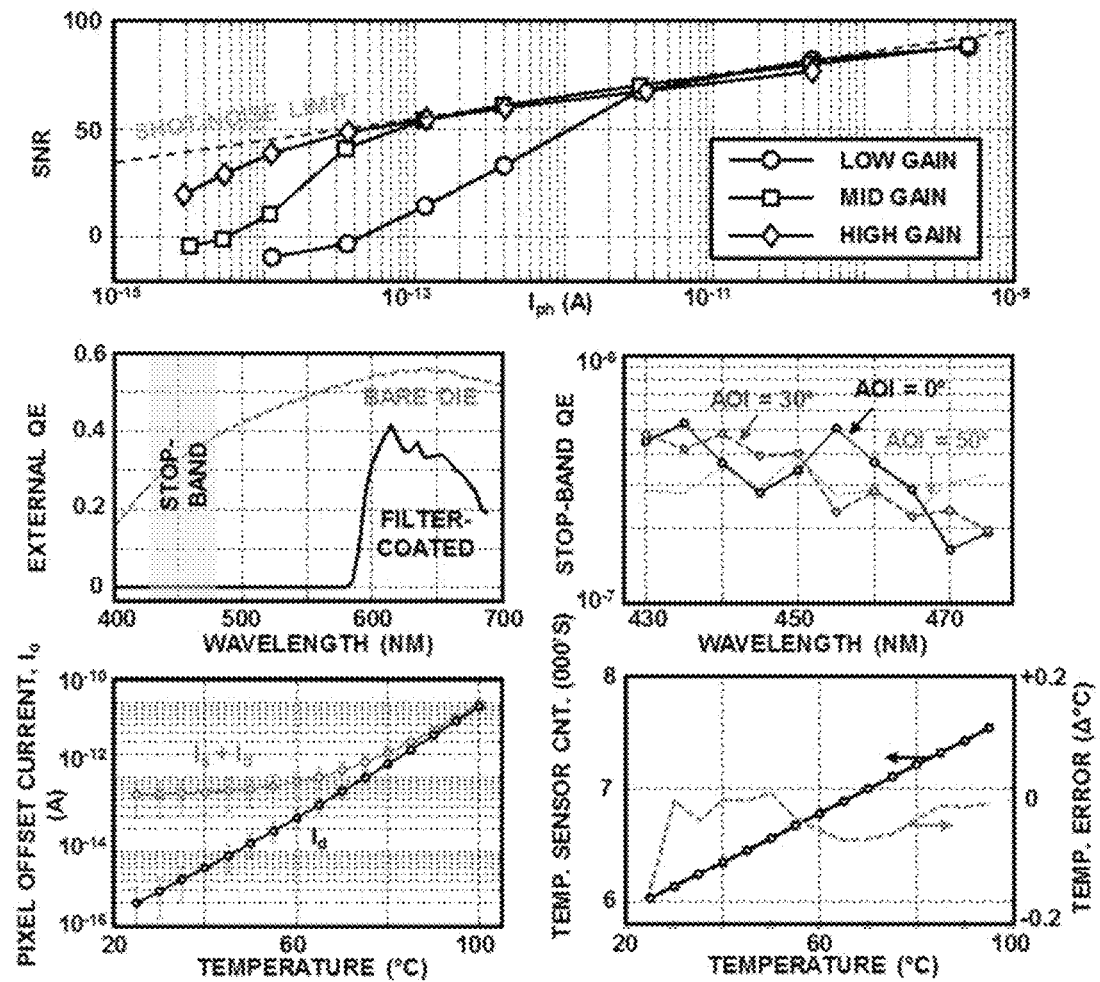
FIG. 12 shows measured primary electrical and optical performances of an example TGF pixel in accordance with one of the embodiments of the present disclosure.

The electrical and optical measurements for this biochip are reported in FIG. 12. The measured signal-to-noise ratio (SNR) from pixels is demonstrate that the added sensor noise is ~30% of the shot-noise when the quantization noise is not limiting within the 100 fA to 1 nA input current region. The total dual-depletion region (DDR) is 137 dB (1.33 fA-10 nA) for $f_s=1.667$ Hz. The photodiode external quantum efficiency (QE), with and without the integrated emission filter, show the pass-band and stop-band QE of 0.4 and $3.69\times10^{-7}$ (OD~5.8), respectively. The measured distribution of $I_{dc}$ and $I_o$ validate the expected randomness with maximum amplitude of 100 pA (<1% of the full scale. The output of the temperature sensor as a function of temperature are also reported in FIG. 12, which shows that with 2-point calibration accuracy of ±0.25° C. is achievable across the 25° C.-100° C. temperature range.

Figure 13:
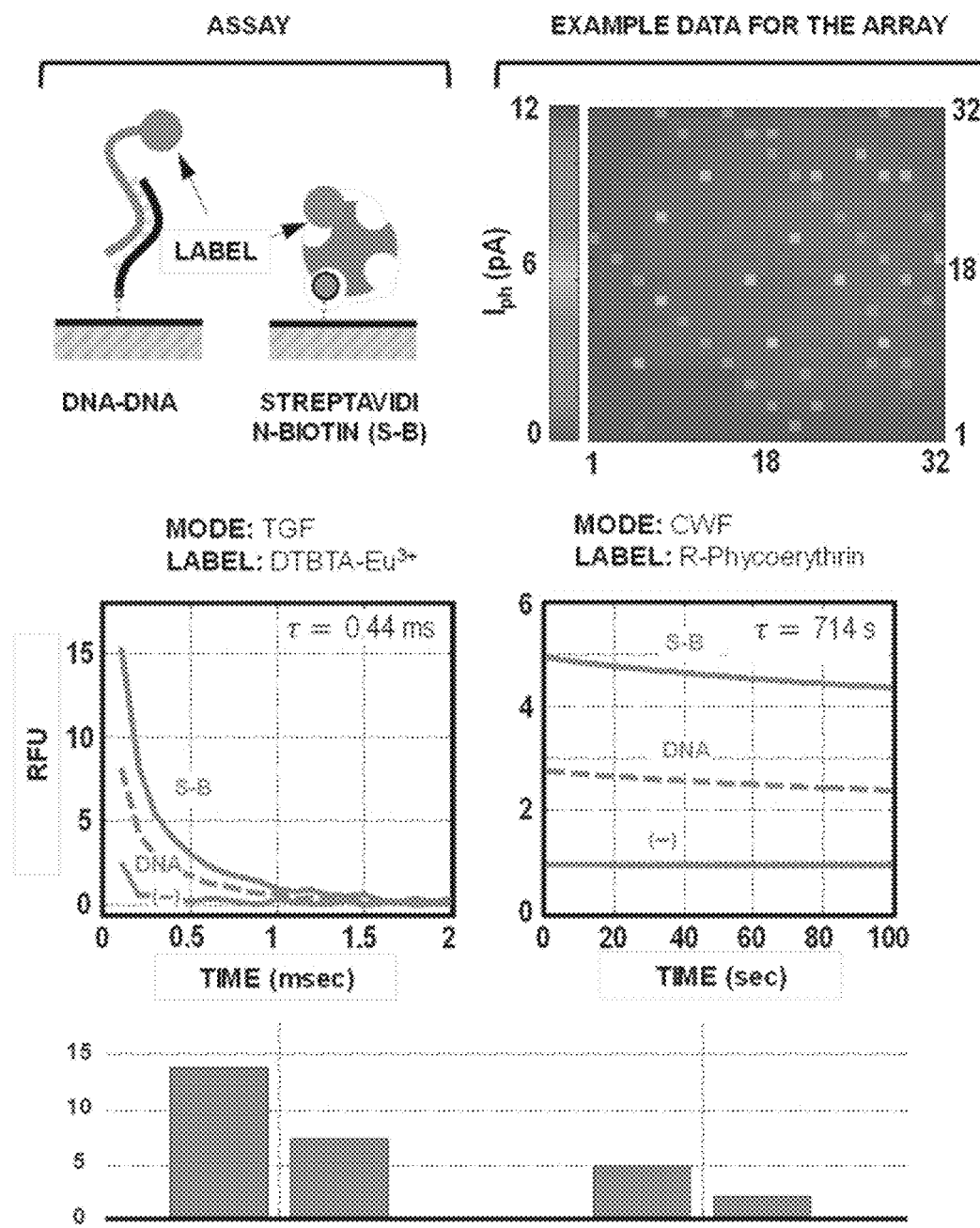
FIG. 13 shows signal-to-background and kinetics measurements for CWF and TGF modes in accordance with one of the embodiments of the present disclosure.

In FIG. 13, the results from two (2) biosensing experiments are reported and compared, to demonstrate the different modes of operation. In all experiments, identical surface functionalization and array-based DNA hybridization or ligand-receptor bindings are performed. However, distinct molecular labels are attached to the targets, for CWF and TGF, respectively. In CWF, using a R-phycoerythrin fluorophore, the signal-to-background (S/B) shows the lowest value. This may be due to the non-ideal blocking of the excitation light. The S/B is increased significantly when using TGF and DTBTA-Eu3+, which is a Europium (Lanthanide) chelate-based long lifetime fluorophore. As evident, the background photon emission from the pulsed light-emitting diode (LED) excitation source decays significantly within 100 μs and the background becomes much smaller than compared to CWF mode.

Figure 14:
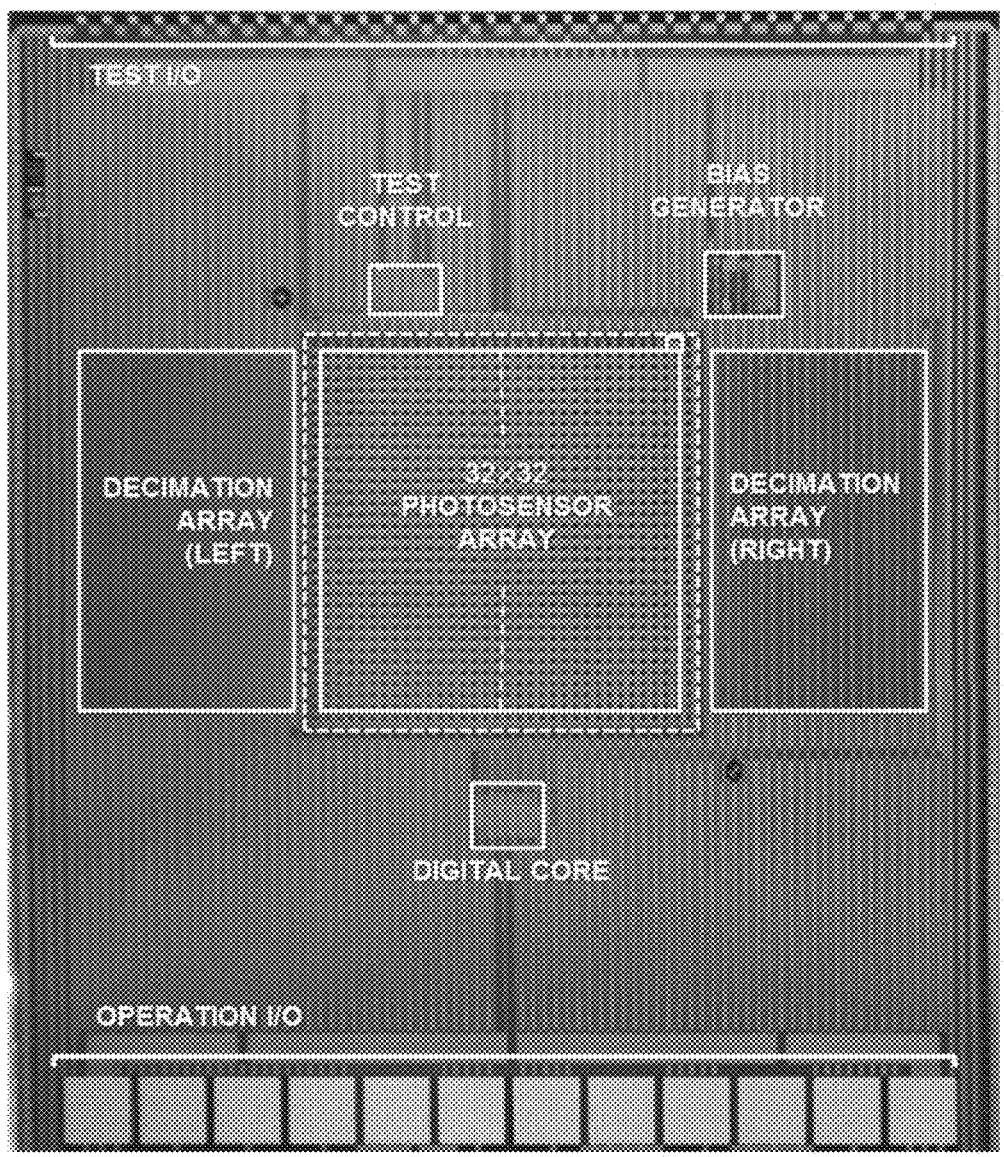
FIG. 14 shows die micrograph of an example TGF CMOS biochip in accordance with one of the embodiments of the present disclosure.

In FIG. 14, the micrograph of the implemented TGF biochip is shown.

Example 2

This example shows how PCI-TGF pixels can be designed in applications where high-density biosensor pixels arrays are required, such as DNA SBS and DNA SBH systems. The example also shows how miniaturized PCI-TGF pixels can be incorporated into standard high-density image sensor arrays. As the example shows, PCI can be added into the circuitry of multi-million pixel CMOS image sensors that can have sub-micron pixel dimensions.

Figures 15A, 15B:
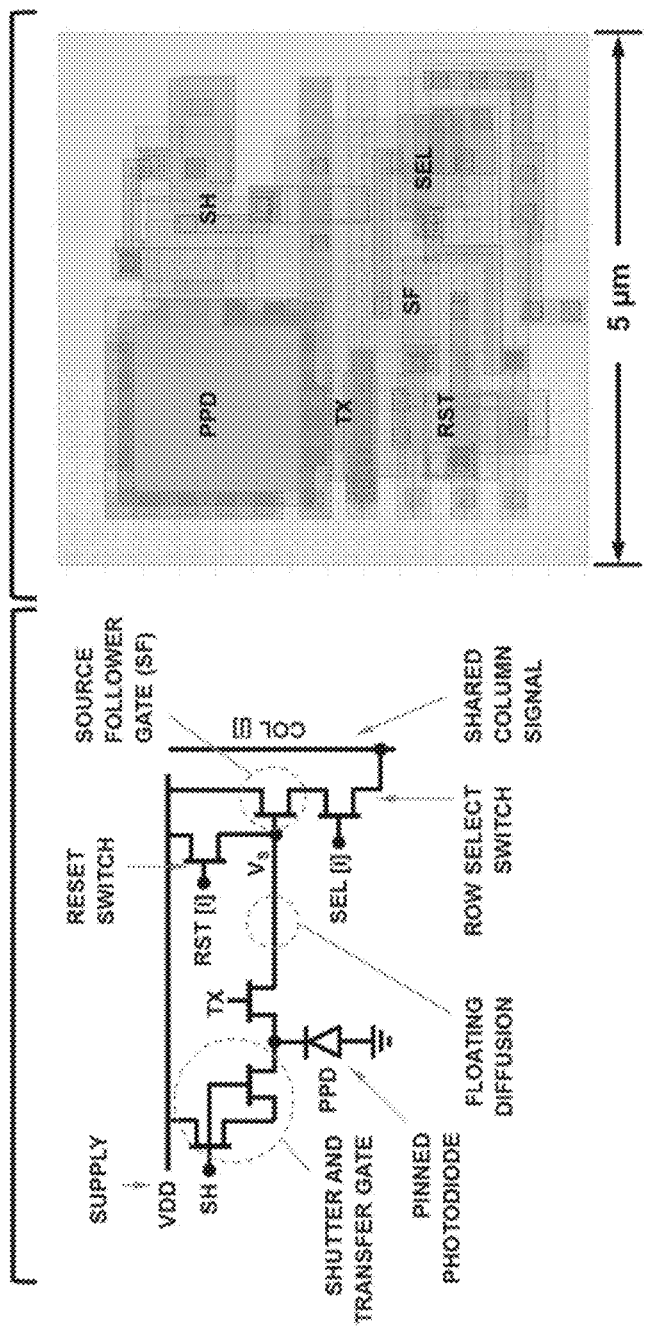
FIG. 15A illustrates circuit schematic of an example six transistor (6T) PCI-TGF pixel in accordance with one of the embodiments of the present disclosure.
FIG. 15B shows the layout of the pixel of FIG. 15A in sub-micron dimensions.

FIG. 15A depicts the circuit diagram example of a six transistor (6T) pixel topology which includes a pinned photodiode (PPD) as the PCT, and two (2) charge transfer gates; one to transfer charge to the sense node (TX) acting as an integrating switch, and one to act as an electronic shutter (SH). The charge is integrated on the floating diffusion (acting as the CIE+CVT) and the generated voltage $V_s$ is read using the source follower gate. In this depiction, we assume that the pixel is located at the (i,j) coordinate within a photo-sensor array and $V_s$ can be accessed by the column signal (COL[j]) by activating the row select signal (SEL[i]). The charge is the floating diffusion can be reset using RST[i].

In FIG. 15B, the layout of this pixel is shown that can be scaled down to sub-micron dimensions similar to equivalent CMOS image sensor pixels.

Figure 16:
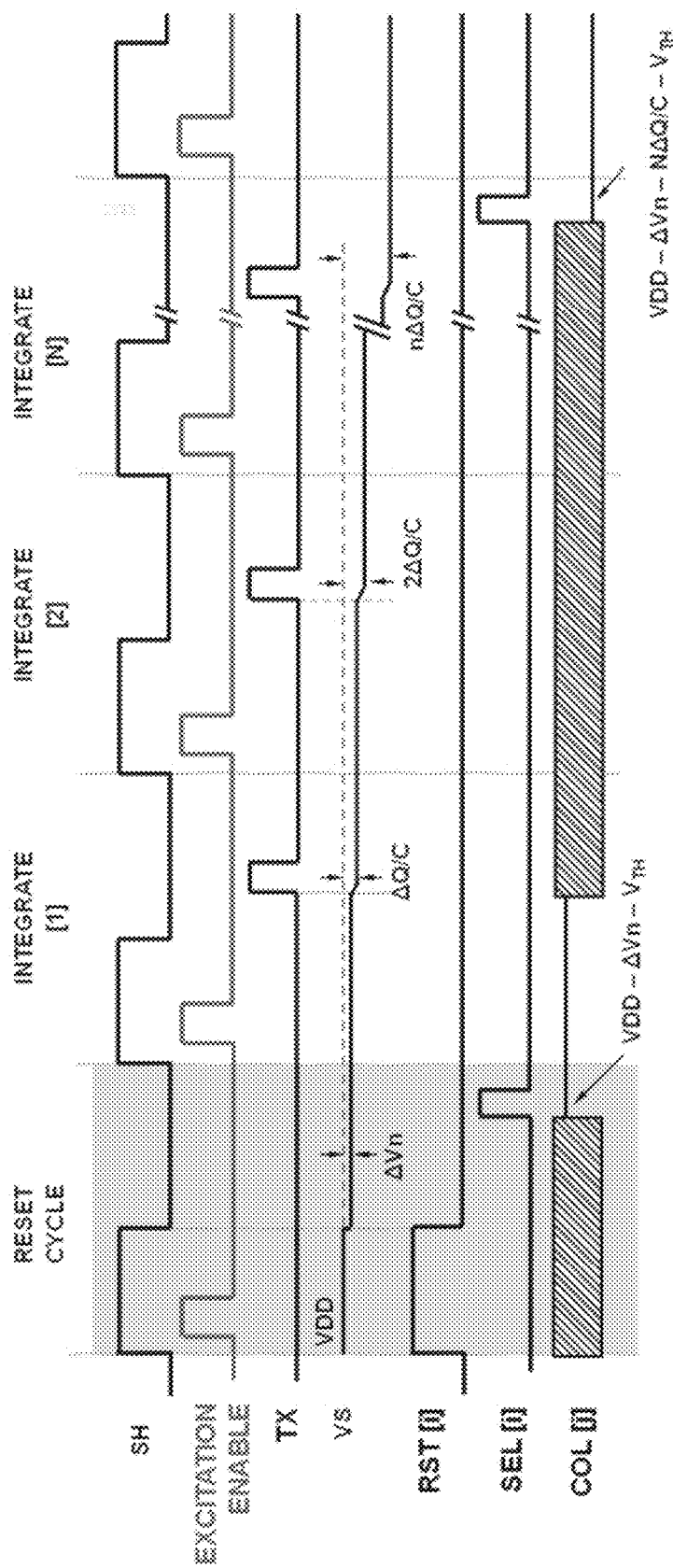
FIG. 16 shows timing diagram of an example PCI-TGF pixel in accordance with one of the embodiments of the present disclosure in which correlated double sampling (CDS) is implemented by reading $V_S$ in the reset cycle and after N PCI cycles.

In FIG. 16, the diagram of the PCI-TGF pixel is shown. As FIG. 16 shows, correlated double sampling (CDS) can be implemented by reading V in the reset cycle and after N PCI cycles. As shown in the reset cycle, the output of the pixel is $V_{DD}-\Delta V_n-V_{th}$, where $\Delta V_n$ and $V_{th}$ are the offset and threshold voltages of the source follower transistor, respectively. Now, at the end of the $N^{th}$ integration cycle, $V_S=V_{DD}-\Delta V_n-V_{th}-N\Delta Q/C$, where $\Delta Q$ is the charge collected by the emission from an individual excitation pulse and C is the floating diffusion effective capacitance. Therefore, by subtracting these two values (i.e., CDS) we can have a value that follows the PCI schemes while is independent of the offset of the source follower that may vary from pixel to pixel within the array.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A device for detecting a presence or absence of an analyte in a solution, comprising:
   a reaction chamber configured to receive and retain said solution; and
   a biochip in direct contact with said reaction chamber and synchronized with a pulsed excitation source operably coupled to said biochip, said biochip comprising:

a surface layer comprising at least one immobilized capture probe that is specific for said analyte;
an electronic shutter, at least one transducer, and at least one integrator; and
circuitry that is configured to:
(i) collect an optical signal from said surface layer generated upon exposure of said surface layer to an excitation pulse,
(ii) convert said optical signal to an electrical signal using said at least one transducer,
(iii) selectively discard said optical signal or said electrical signal converted in (ii) using said electronic shutter;
(iv) integrate said electrical signal periodically using said at least one integrator; and
(v) generate an output electrical signal derived at least in part from said electrical signal integrated in (iv), wherein said output electrical signal is indicative of said presence or absence of said analyte.

2. The device of claim 1, wherein said device comprises a plurality of individually addressable locations disposed within said reaction chamber,
wherein said plurality of individually addressable locations comprises at least a first location comprising a first immobilized capture probe and a second location comprising a second immobilized probe different from said first immobilized probe,
wherein said electronic shutter, said transducer, and said integrator are disposed at said first location of said plurality of individually addressable locations; and
wherein an additional electronic shutter, an additional transducer, and an additional integrator are disposed at said second location of said plurality of individually addressable locations.

3. The device of claim 2, wherein said plurality of independently addressable locations comprises greater than or equal to about 100 locations, 1,000 locations, or 100,000 locations.

4. The device of claim 1, wherein said electronic shutter comprises an electronic shutter switch operably coupled to said at least one transducer, which electronic shutter switch is configured to facilitate said discarding of said optical signal or said converted electrical signal from said at least one transducer upon application of a voltage control signal to said electronic shutter switch.

5. The device of claim 1, wherein said sensor further comprises at least one integration switch disposed between and operably coupled to said at least one transducer and said at least one integrator, wherein said at least one integration switch is configured to transfer said electrical signal from said at least one transducer to said at least one integrator.

6. The device of claim 1, wherein said sensor further comprises at least one additional transducer operably coupled to said at least one integrator, which said at least one additional transducer is configured to convert said electrical signal integrated by said at least one integrator to said output electrical signal.

7. The device of claim 1, wherein said electrical signal comprises photo-induced charge, and wherein said output electrical signal comprises voltage.

8. The device of claim 1, wherein said device is included in a complementary metal oxide semiconductor (CMOS) integrated circuit (IC).

9. The device of claim 1, wherein said output electrical signal is derived at least in part from an optical signal produced by a label associated with said analyte upon binding of said analyte to said at least one probe.

10. The device of claim 9, wherein said label is a fluorophore.

11. The device of claim 1, wherein said output electrical signal is derived at least in part from an optical signal or change thereof from said at least one probe or said analyte upon binding of said analyte to said at least one probe.

12. The device of claim 11, wherein said at least one probe comprises an energy donor and said analyte comprises an energy acceptor.

13. The device of claim 12, wherein said energy donor is a fluorophore, and wherein said energy acceptor is an additional fluorophore or a quencher.

14. The device of claim 1, wherein said reaction chamber comprises at least one control probe, and wherein said electronic shutter, said at least one transducer, and said at least one integrator are configured to collect a control signal from said at least one control probe and normalize said collected optical signal using said control signal.

15. The device of claim 14, wherein said at least one control probe does not bind to or interact with said analyte.

16. The device of claim 1, further comprising a controllable fluidic unit, a temperature control unit, and a digital unit.

17. The device of claim 16, wherein said controllable fluidic unit is configured to transfer at least a portion of said solution into or out of said reaction chamber.

18. The device of claim 16, wherein said digital unit is configured to receive or store said output electrical signal from said device.

19. The device of claim 1, wherein said sensor is configured to repeat (i)-(iv) multiple times prior to (v).

20. The device of claim 19, wherein said output electrical signal is a single output.

21. The device of claim 1, wherein said reaction chamber is integrated with at least one of said electrical shutter, said transducer, or said integrator.

22. The device of claim 1, wherein said at least one integrator comprises a capacitive trans-impedance amplifier (CTIA).

23. A method for detecting a presence or absence of an analyte in a solution, comprising:
(a) directing said solution to a device comprising:
a reaction chamber configured to receive and retain said solution, and
a biochip in direct contact with said reaction chamber and synchronized with a pulsed excitation source operably coupled to said biochip, said biochip comprising:
a surface layer comprising at least one immobilized capture probe that is specific for said analyte,
an electronic shutter, a transducer and an integrator operably coupled to one another;
(b) using said transducer to convert an optical signal to an electrical signal, wherein said optical signal is generated upon exposure of said surface layer to said pulsed excitation source;
(c) selectively discarding said optical signal or said electrical signal converted in (b) within a first time period;
(d) using said integrator to integrate said electrical signal within a second time period different from said first time period to thereby generate an output signal which is indicative of said presence or absence of said analyte.

24. The method of claim 23, further comprising, repeating (b)-(d) one or more times.

25. The method of claim 24, wherein said one or more times comprise greater than or equal to about 100 times.

26. A method for determining a presence or absence of an analyte in solution, comprising:
(a) directing said solution to a device comprising:
a reaction chamber configured to receive and retain said solution; and
a biochip in direct contact with said reaction chamber and synchronized with a pulsed excitation source operably coupled to said biochip, said biochip comprising (i) a surface layer comprising at least one immobilized capture probe that is specific for said analyte, and (ii) a sensing layer;
(b) using said sensing layer to collect optical signals periodically from said surface layer each time when said pulsed excitation source is off, wherein said optical signals are generated upon exposure of said surface layer to said pulsed excitation source and collected without the use of an optical filter;
(c) integrating said signals derived from optical signals to generate a single output signal indicative of said presence or absence of said analyte; and
(d) determining said presence or absence of said analyte based on said single output signal.

\* \* \* \* \*